(12) United States Patent
Barth et al.

(10) Patent No.: US 7,541,361 B2
(45) Date of Patent: Jun. 2, 2009

(54) N-[4,5-DIPHENYLPYRIMIDIN-2-YL)METHYL]AMINE DERIVATIVES, THE PREPARATION THEREOF AND THEIR THERAPEUTIC USE

(75) Inventors: Francis Barth, Saint Georges d'Orques (FR); Christian Congy, Saint Gely du Fese (FR); Patrick Gueule, Teyran (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/968,855

(22) Filed: Jan. 3, 2008

(65) Prior Publication Data

US 2008/0176867 A1    Jul. 24, 2008

Related U.S. Application Data

(63) Continuation of application No. PCT/FR2006/001621, filed on Jul. 6, 2006.

(30) Foreign Application Priority Data

Jul. 8, 2005    (FR) .................... 05 07359

(51) Int. Cl.
- C07D 239/26    (2006.01)
- C07D 403/12    (2006.01)
- C07D 403/14    (2006.01)
- A61K 31/505    (2006.01)
- A61K 31/506    (2006.01)
- A61P 3/04    (2006.01)

(52) U.S. Cl. ...................... 514/256; 544/242

(58) Field of Classification Search ............... 544/242; 514/256

See application file for complete search history.

(56) References Cited

FOREIGN PATENT DOCUMENTS

| WO | WO 92/02513 | 2/1992 |
| WO | WO 2004/029204 | 4/2004 |
| WO | WO 2004/110453 | 12/2004 |

OTHER PUBLICATIONS

Petrocellis et al., British Journal of Pharmacology, 141, 765-774, 2004.*
Black, Curr. Opin.. Investig. Drugs 5(4): 389-394, 2004 (PubMed Abstract provided).*

* cited by examiner

*Primary Examiner*—Venkataraman Balasubramanian
(74) *Attorney, Agent, or Firm*—Balaram Gupta

(57) ABSTRACT

The invention relates to compounds of formula (I):

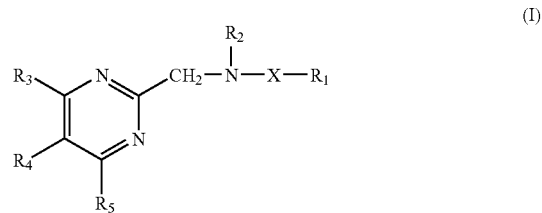

Wherein X, $R_1$, $R_2$, $R_3$, $R_4$ and $R_5$ are as defined herein. The invention also relates to a method for preparing the aforementioned compounds and to their therapeutic use.

16 Claims, No Drawings

N-[(4,5-DIPHENYLPYRIMIDIN-2-YL)METHYL]AMINE DERIVATIVES, THE PREPARATION THEREOF AND THEIR THERAPEUTIC USE

This application is a continuation of International application No. PCT/FR2006/001,621, filed Jul. 6, 2006, which is incorporated herein by reference in its entirety; which claims the benefit of priority of French Patent Application No. 05/07, 359, filed Jul. 8, 2005.

The present invention relates to substituted derivatives of N-[(4,5-diphenylpyrimidin-2-yl)methyl]amine, their preparation and their application in therapeutics.

Diphenylpyrazole derivatives with affinity for the $CB_1$ cannabinoid receptors have been described notably in patents U.S. Pat. No. 5,624,941, EP 0 576 357, EP 0 656 354, EP 1 150 961.

Derivatives of 4,5-diarylpyrimidine as ligands for the cannabinoid receptors are described in international application WO 2004/110453 or in international application WO 2004/029204.

Derivatives of 4,5-bis[($C_1$-$C_6$)alkoxyphenyl]pyrimidine possessing antithrombotic, vasodilatory and anti-inflammatory activity are described in international application WO 92/02513.

Novel substituted derivatives of N-[(4,5-diphenylpyrimidin-2-yl)methyl]amine have now been found which possess $CB_1$ cannabinoid receptor antagonist properties, localized at the central and/or peripheral level.

The present invention relates to compounds corresponding to the formula:

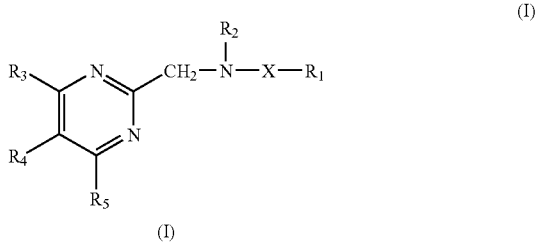

(I)

in which:
X represents a group

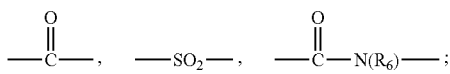

$R_1$ represents:
a ($C_1$-$C_{12}$)-alkyl, unsubstituted or substituted one or more times with substituents selected independently from a fluorine atom, a hydroxyl, a ($C_1$-$C_4$)-alkoxy, a ($C_1$-$C_4$)-alkylthio, a phenoxy, a trifluoromethoxy radical, a difluoromethoxy radical, a difluoromethylthio radical, a trifluoromethylthio radical;
a non-aromatic ($C_3$-$C_{12}$) carbocyclic radical, unsubstituted or substituted one or more times with substituents selected independently from a ($C_1$-$C_4$)-alkyl, a ($C_1$-$C_4$)-alkoxy, a fluorine atom, a hydroxyl, a trifluoromethyl radical, a trifluoromethoxy radical, a ($C_1$-$C_4$)-alkylthio;
a ($C_3$-$C_7$)-cycloalkylmethyl, unsubstituted or substituted one or more times on the carbocycle with substituents selected independently from a ($C_1$-$C_4$)-alkyl, a ($C_1$-$C_4$)-alkoxy, a fluorine atom, a hydroxyl, a trifluoromethyl radical, a trifluoromethoxy radical;
a phenyl, unsubstituted or substituted one or more times with substituents selected independently from a halogen atom, a hydroxyl, an Alk group, an OAlk group, a methylenedioxy, a ($C_1$-$C_4$)-alkylamino, a di-($C_1$-$C_4$)-alkylamino, a cyano, a nitro, an $S(O)_n$Alk group, an $OS(O)_n$ Alk group, a ($C_1$-$C_4$)-alkylcarbonyl group; or from a phenyl, phenoxy, pyrrolyl, imidazolyl, pyridyl or pyrazolyl radical, said radical being unsubstituted or substituted one or more times with a ($C_1$-$C_4$)-alkyl;
a benzyl, unsubstituted or substituted one or more times on the phenyl with substituents selected independently from a halogen atom, an Alk group, a hydroxyl, an OAlk group, a methylenedioxy, an $S(O)_n$Alk group, an $OS(O)_n$ Alk group and unsubstituted or substituted on alpha by one or two similar or dissimilar groups selected from a ($C_1$-$C_4$)-alkyl, a ($C_3$-$C_7$)-cycloalkyl;
a phenethyl, unsubstituted or substituted one or more times on the phenyl with substituents selected independently from a halogen atom, a ($C_1$-$C_4$)-alkyl, a ($C_1$-$C_4$)-alkoxy, a trifluoromethyl radical, a trifluoromethoxy radical;
a benzhydryl; a benzhydrylmethyl;
a 1,2,3,4-tetrahydronaphthalenyl, unsubstituted or substituted one or more times with a ($C_1$-$C_4$)-alkyl;
an aromatic heterocyclic radical selected from pyrrolyl, imidazolyl, furyl, thienyl, pyrazolyl, oxazolyl, pyridyl, indolyl, said radical being unsubstituted or substituted one or more times with substituents selected independently from a halogen atom or a ($C_1$-$C_4$)-alkyl, a ($C_1$-$C_4$)-alkoxy, a trifluoromethyl radical, a trifluoromethoxy radical, a cyano, a nitro, a ($C_1$-$C_4$)-alkylthio;
$R_2$ represents a hydrogen atom or a ($C_1$-$C_3$)-alkyl;
$R_3$ represents a hydrogen atom or a ($C_1$-$C_5$)-alkyl;
$R_4$ represents a phenyl, unsubstituted or substituted one or more times with substituents selected independently from a halogen atom, Alk group, OAlk group, $S(O)_n$Alk group or $OS(O)_n$Alk group;
$R_5$ represents a phenyl, unsubstituted or substituted one or more times with substituents selected independently from a halogen atom, Alk group, OAlk group, $S(O)_n$Alk group or $OS(O)_n$Alk group;
$R_6$ represents a hydrogen atom or a ($C_1$-$C_3$)-alkyl;
n represents 0, 1 or 2;
Alk represents a ($C_1$-$C_4$)-alkyl, unsubstituted or substituted one or more times with a fluorine atom; with the proviso that $R_4$ and $R_5$ do not simultaneously represent a phenyl substituted with a ($C_1$-$C_4$)-alkoxy.

The compounds of formula (I) can contain one or more asymmetric carbon atoms. They can therefore be in the form of enantiomers or of diastereoisomers. These enantiomers, diastereoisomers as well as mixtures thereof, including the racemic mixtures, form part of the invention.

The compounds of formula (I) can be in the form of hydrates or solvates, i.e. in the form of associations or combinations with one or more water molecules or with a solvent. Such hydrates and solvates also form part of the invention.

"Halogen atom" means an atom of bromine, chlorine, fluorine or iodine.

The terms ($C_1$-$C_3$)-alkyl or respectively ($C_1$-$C_4$)-alkyl, ($C_1$-$C_5$)-alkyl or ($C_1$-$C_{12}$)-alkyl mean a linear or branched alkyl radical with one to three carbon atoms or respectively with one to four carbon atoms, one to five carbon atoms or one to twelve carbon atoms, such as the methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl radical.

($C_1$-$C_4$)-alkoxy means a linear or branched alkoxy radical with one to four carbon atoms such as the methoxy, ethoxy, propoxy, isopropoxy, butoxy, sec-butoxy, tert-butoxy radical.

($C_3$-$C_7$)-cycloalkyl means a cyclic alkyl group with 3 to 7 carbon atoms, such as the cyclopropyl, cyclobutyl, cyclopentyl, cyclohexyl, cycloheptyl group.

The non-aromatic $C_3$-$C_{12}$ carbocyclic radicals comprise the mono- or polycyclic, condensed, bridged or spiro radicals. The monocyclic radicals include the cycloalkyls for example cyclopropyl, cyclobutyl, cyclopentyl, cyclohexyl, cycloheptyl, cyclooctyl. The di- or tricyclic condensed, bridged or spiro radicals include for example the norbornyl, bornyl, isobornyl, noradamantyl, adamantyl, spiro[5.5]undecyl, bicyclo[2.2.1]heptyl, bicyclo[3.2.1]octyl; bicyclo[3.1.1]heptyl radicals.

Among the compounds of formula (I) that are objects of the invention, we may mention in particular the compounds of formula (I) in which:

X represents a group

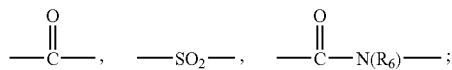

$R_1$ represents:
a ($C_1$-$C_7$)-alkyl;
a non-aromatic ($C_3$-$C_{12}$) carbocyclic radical, unsubstituted or substituted one or more times with a ($C_1$-$C_4$)-alkyl;
a ($C_3$-$C_7$)-cycloalkylmethyl, unsubstituted or substituted one or more times on the carbocycle with a ($C_1$-$C_4$)-alkyl;
a phenyl, unsubstituted or mono-, di- or tri-substituted with substituents selected independently from a halogen atom, a ($C_1$-$C_4$)-alkyl, a ($C_1$-$C_4$)-alkoxy, a ($C_1$-$C_4$)-alkylamino, a di-($C_1$-$C_4$)-alkylamino, a cyano, a trifluoromethyl radical, a trifluoromethoxy radical, an S(O)$_n$Alk group, a ($C_1$-$C_4$)-alkylcarbonyl group; or from a phenyl, phenoxy, pyrrolyl, imidazolyl, pyridyl or pyrazolyl radical, said radicals being unsubstituted or substituted one or more times with a ($C_1$-$C_4$)-alkyl;
a benzyl, unsubstituted or mono- or disubstituted on the phenyl with substituents selected independently from a halogen atom, a ($C_1$-$C_4$)-alkyl, a ($C_1$-$C_4$)-alkoxy, a trifluoromethyl radical;
a benzhydryl; a benzhydrylmethyl;
an aromatic heterocyclic radical selected from pyrrolyl, imidazolyl, furyl, thienyl, pyrazolyl, indolyl unsubstituted or substituted one or more times with substituents selected independently from a halogen atom or a ($C_1$-$C_4$)-alkyl;
$R_2$ represents a hydrogen atom or a ($C_1$-$C_3$)-alkyl;
$R_3$ represents a hydrogen atom or a ($C_1$-$C_5$)-alkyl;
$R_4$ represents a phenyl, unsubstituted or mono-, di- or tri-substituted with substituents selected independently from a halogen atom, a ($C_1$-$C_4$)-alkyl, a ($C_1$-$C_4$)-alkoxy, a trifluoromethyl radical or an S(O)$_n$Alk group;
$R_5$ represents a phenyl, unsubstituted or mono-, di- or tri-substituted with substituents selected independently from a halogen atom, a ($C_1$-$C_4$)-alkyl, a ($C_1$-$C_4$)-alkoxy, a trifluoromethyl radical or an S(O)$_n$Alk group;
$R_6$ represents a hydrogen atom or a ($C_1$-$C_3$)-alkyl;
n represents 0, 1 or 2;
Alk represents a ($C_1$-$C_4$)-alkyl;
with the proviso that $R_4$ and $R_5$ do not simultaneously represent a phenyl substituted with a ($C_1$-$C_4$)-alkoxy.

Among the compounds of formula (I) that are objects of the invention, a distinction is made between:
the compounds of formula (IA) in which —X— represents a —CO— radical and the substituents $R_1$ to $R_5$ are as defined for the compounds of formula (I);
the compounds of formula (IB) in which —X— represents an —SO$_2$— radical and the substituents $R_1$ to $R_5$ are as defined for the compounds of formula (I);
the compounds of formula (IC) in which —X— represents a —CON($R_6$)— radical and the substituents $R_1$ to $R_6$ are as defined for the compounds of formula (I).

Among the compounds of formula (I) that are objects of the invention, a first group of compounds comprises the compounds for which:
X is as defined for a compound of formula (I);
$R_1$ represents:
a ($C_1$-$C_7$)-alkyl;
a ($C_3$-$C_7$)-cycloalkyl; a norbornyl;
a phenyl, unsubstituted or mono- or disubstituted with substituents selected independently from a halogen atom, a ($C_1$-$C_4$)-alkyl, a ($C_1$-$C_4$)-alkoxy, a di-($C_1$-$C_4$)-alkylamino, a nitro, a trifluoromethyl radical, a difluoromethoxy radical, a phenyl, a phenoxy, a pyrrolyl;
a benzyl, unsubstituted or substituted with a trifluoromethyl radical;
a benzhydrylmethyl;
an aromatic heterocyclic radical selected from a pyrazolyl, a furyl, a thienyl, an indolyl, unsubstituted or substituted once or twice with substituents selected independently from a halogen atom or a ($C_1$-$C_4$)-alkyl;
and/or $R_2$ represents a hydrogen atom;
and/or $R_3$ represents a hydrogen atom or a methyl;
and/or $R_4$ represents a phenyl substituted with a halogen atom or a ($C_1$-$C_4$)-alkoxy;
and/or $R_5$ represents a phenyl mono- or disubstituted with a halogen atom;
and/or $R_6$ represents a hydrogen atom;

as well as their hydrates or their solvates.

Among the compounds of this last-mentioned group, we may mention the compounds of formula (I) for which:
X is as defined for a compound of formula (I);
$R_1$ represents:
a 1-ethylpropyl; a 1-propylbutyl;
a cyclopentyl; a cyclohexyl; a cycloheptyl; a 2-norbornyl;
a phenyl; a 4-bromophenyl; a 3-chlorophenyl; a 4-chlorophenyl; a 2-fluorophenyl; a 3-fluorophenyl; a 3,5-difluorophenyl; a 4-tert-butylphenyl; a 3,5-dimethylphenyl; a 3-methoxyphenyl; a 4-(diethylamino)phenyl; a 3-(trifluoromethyl)phenyl; a 4-(trifluoromethyl)phenyl; a 2-chloro-4-(trifluoromethyl)phenyl; a 2-nitro-4-(trifluoromethyl)phenyl; a 2-bromo-4-(trifluoromethyl)phenyl; a 2-fluoro-5-(trifluoromethyl)phenyl; a 4-fluoro-3-(trifluoromethyl)phenyl; a 2-chloro-5-(trifluoromethyl)phenyl; a 4-(difluoromethoxy)phenyl; a biphenyl-2-yl; a 3-phenoxyphenyl; a 4-phenoxyphenyl; a 4-(1H-pyrrol-1-yl)phenyl;
a 3-(trifluoromethyl)benzyl;
a benzhydrylmethyl;
a 2-thienyl; a 5-chloro-2-thienyl; a 5-bromo-2-furyl; a 3-tert-butyl-1-ethyl-1H-pyrazol-5-yl; a 1H-indol-2-yl; a 1-methyl-1H-indol-2-yl;
$R_2$ represents a hydrogen atom;
$R_3$ represents a hydrogen atom or a methyl;
$R_4$ represents a 4-bromophenyl; a 4-chlorophenyl; a 4-methoxyphenyl;
$R_5$ represents a 2,4-dichlorophenyl;

$R_6$ represents a hydrogen atom;

as well as their hydrates or their solvates.

Among the compounds of this last-mentioned group, we may mention the compounds of formula (I) for which:

X represents a —CO— or —SO$_2$— group;

$R_1$ represents:
a 3-(trifluoromethyl)phenyl; a 4-(trifluoromethyl)phenyl; a 2-chloro-4-(trifluoromethyl)phenyl; a 3-phenoxyphenyl; a 4-(1H-pyrrol-1-yl)phenyl;

a benzhydrylmethyl;

$R_2$ represents a hydrogen atom;

$R_3$ represents a hydrogen atom or a methyl;

$R_4$ represents a 4-bromophenyl or a 4-methoxyphenyl;

$R_5$ represents a 2,4-dichlorophenyl;

as well as their hydrates or their solvates.

Among the compounds of formula (I) that are objects of the invention, we may notably mention the following compounds:

N-[[5-(4-bromophenyl)-4-(2,4-dichlorophenyl)pyrimidin-2-yl]methyl]-3-(trifluoromethyl)benzenesulfonamide;

N-[[5-(4-bromophenyl)-4-(2,4-dichlorophenyl)pyrimidin-2-yl]methyl]-4-(trifluoromethyl)benzenesulfonamide;

N-[[4-(2,4-dichlorophenyl)-5-(4-methoxyphenyl)pyrimidin-2-yl]methyl]-4-(1H-pyrrol-1-yl)benzamide;

N-[[5-(4-bromophenyl)-4-(2,4-dichlorophenyl)pyrimidin-2-yl]methyl]-3,3-diphenylpropanamide;

N-[[5-(4-bromophenyl)-4-(2,4-dichlorophenyl)-6-methylpyrimidin-2-yl]methyl]-3,3-diphenylpropanamide;

N-[[5-(4-bromophenyl)-4-(2,4-dichlorophenyl)-6-methylpyrimidin-2-yl]methyl]-3-(trifluoromethyl)benzenesulfonamide;

N-[[5-(4-bromophenyl)-4-(2,4-dichlorophenyl)-6-methylpyrimidin-2-yl]methyl]-4-(trifluoromethyl)benzenesulfonamide;

N-[[5-(4-bromophenyl)-4-(2,4-dichlorophenyl)-6-methylpyrimidin-2-yl]methyl]-2-chloro-4-(trifluoromethyl)benzenesulfonamide;

N-[[5-(4-bromophenyl)-4-(2,4-dichlorophenyl)-6-methylpyrimidin-2-yl]methyl]-3-phenoxybenzenesulphonamide;

as well as their hydrates or their solvates.

"Leaving group" means, hereinafter, a group that can be easily cleaved from a molecule by rupture of a hydrolytic bond, with departure of an electron pair. This group can thus easily be replaced by another group in a substitution reaction, for example. Such leaving groups are, for example, the halogens or an activated hydroxy group such as a methanesulfonate, benzenesulfonate, p-toluenesulfonate, triflate, acetate, etc. Examples of leaving groups as well as references for their preparation are given in "Advances in Organic Chemistry", J. March, 3rd edition, Wiley Interscience, 1985, p. 310-316.

In accordance with the invention, the compounds of formula (I) can be prepared according to a method that is characterized in that: a compound of formula:

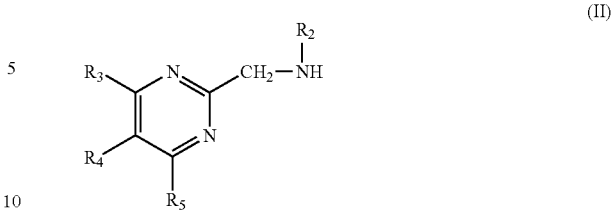

in which $R_2$, $R_3$, $R_4$ and $R_5$ are as defined for a compound of formula (I)

is treated
either with an acid or a functional derivative of that acid of formula:

in which $R_1$ is as defined for a compound of formula (I), when it is necessary to prepare a compound of formula (I) in which —X— represents a —CO— group;

or with a sulfonyl halide of formula:

in which $R_1$ is as defined for a compound of formula (I) and Hal represents a halogen atom, preferably chlorine, when it is necessary to prepare a compound of formula (I) in which —X— represents an —SO$_2$— group;

or with a haloformate of formula:

in which Hal represents a halogen atom and Ar represents a phenyl or a 4-nitrophenyl to obtain an intermediate of formula:

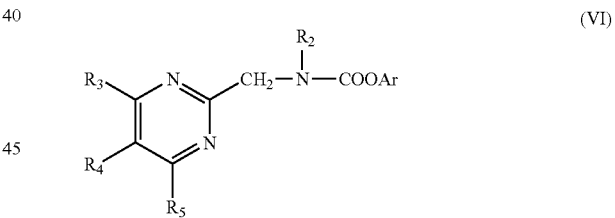

in which $R_2$, $R_3$, $R_4$ and $R_5$ are as defined for a compound of formula (I), which is then reacted with an amine of formula:

in which $R_1$ and $R_6$ are as defined for a compound of formula (I), when it is necessary to prepare a compound of formula (I) in which —X— represents a —CON($R_6$)— group.

When a compound of formula (II) is treated with the acid of formula (III) itself, this is carried out in the presence of a coupling agent used in peptide chemistry such as 1,3-dicyclohexylcarbodiimide or benzotriazol-1-yloxytris(dimethylamino)phosphonium hexafluorophosphate or benzotriazol-1-yloxytris(pyrrolidino)phosphonium hexafluorophosphate or 2-(1H-benzotriazol-1-yl)-1,1,3,3-tetramethyl uronium tetrafluoroborate, in the presence of a base such as triethylamine, N,N-diisopropylethylamine or 4-dimethylaminopyridine, in a solvent such as dichloromethane, dichloroethane, N,N-dimethylformamide or tetrahydrofuran at a temperature between −10° C. and the reflux temperature of the solvent.

As the functional derivative of acid (III), it is possible to use the acid chloride, the anhydride, a mixed anhydride, a $C_1$-$C_4$-alkyl ester in which the alkyl is linear or branched, an activated ester, such as the p-nitrophenyl ester.

Thus, in the method according to the invention, it is also possible to react the acid chloride obtained by reaction of thionyl chloride or oxalyl chloride on the acid of formula (III), with the compound of formula (II), in a solvent, such as a chlorinated solvent (dichloromethane, dichloroethane, chloroform for example), an ether (tetrahydrofuran, dioxan for example), or an amide (N,N-dimethylformamide for example) in an inert atmosphere, at a temperature between 0° C. and room temperature, in the presence of a tertiary amine such as triethylamine, N-methylmorpholine or pyridine.

A variant comprises preparing the mixed anhydride of the acid of formula (III) by reaction of ethyl chloroformate with the acid of formula (III), in the presence of a base such as triethylamine, and reacting it with the compound of formula (II), in a solvent such as dichloromethane, in an inert atmosphere, at room temperature, in the presence of a base such as triethylamine.

When a compound of formula (II) is treated with a sulfonyl halide of formula (IV), this is carried out in the presence of a base such as triethylamine or diisopropylethylamine, in a solvent such as dichloromethane or tetrahydrofuran and at a temperature between room temperature and the reflux temperature of the solvent.

When a compound of formula (II) is treated with a haloformate of formula (V), this is carried out in the presence of a base such as triethylamine, in a solvent such as dichloromethane and at a temperature between 0° C. and room temperature. Then the intermediate of formula (VI) thus obtained is reacted with an amine of formula (VII), in a solvent such as dichloromethane, in the presence of a base such as triethylamine and at a temperature between 0° C. and the reflux temperature of the solvent.

According to a variant of the method, the compounds of formula (I) in which —X— represents a —CON($R_6$)— group in which $R_6$=H can be prepared by reaction of a compound of formula (II) with an isocyanate of formula $R_1$—N=C=O (VIII), in a solvent such as dichloromethane and at a temperature between room temperature and the reflux temperature of the solvent.

According to another variant of the method, the compounds of formula (I) in which —X— represents a —CON($R_6$)— group can be prepared by reaction of a compound of formula (II) with a compound of formula ClCON($R_6$)$R_1$ (IX) in the presence of a base such as triethylamine, in a solvent such as dichloromethane and at a temperature between 0° C. and room temperature.

According to another variant of the method, a compound of formula (I) in which $R_2$ represents a ($C_1$-$C_3$)-alkyl can be prepared by reaction of a compound of formula (I) in which $R_2$=H with a ($C_1$-$C_3$)-alkyl halide, in the presence of a base such as sodium hydride, in a solvent such as N,N-dimethylformamide and at a temperature between room temperature and the reflux temperature of the solvent.

The compounds of formula (I) thus obtained can subsequently be separated from the reaction mixture and purified by conventional methods, for example by crystallization or chromatography.

The compounds of formula (II) are prepared by reaction of a compound of formula:

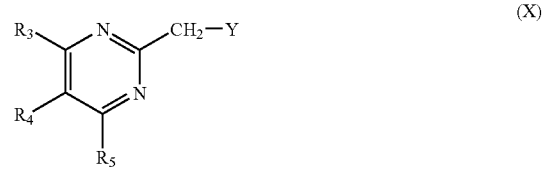

(X)

in which $R_3$, $R_4$ and $R_5$ are as defined for a compound of formula (I) and Y represents a leaving group as defined above, preferably a halogen atom or an activated hydroxy group such as a methanesulfonate, benzenesulfonate, p-toluenesulfonate or triflate group, with a compound of formula:

(XI)

in which $R_2$ is as defined for a compound of formula (I).

The reaction is carried out in a solvent such as N,N-dimethylformamide, acetonitrile, dichloromethane, toluene or propan-2-ol, in the presence of or in the absence of a base. When a base is used, it is selected from the organic bases such as triethylamine, N,N-diisopropylethylamine or N-methylmorpholine. The reaction is carried out at a temperature between 0° C. and the reflux temperature of the solvent.

According to a variant, a compound of formula (II) in which $R_2$=H can also be prepared by reaction of a compound of formula (X) in which Y=Cl with 1,3,5,7-tetraazatricyclo[3.3.1$^{3,7}$]decane (or hexamethylenetetramine) in the presence of an alkali metal halide such as sodium iodide, in a solvent such as ethanol, at a temperature between room temperature and the reflux temperature of the solvent, followed by hydrolysis with a strong acid such as hydrochloric acid.

According to another variant, a compound of formula (II) in which $R_2$=H can also be prepared by reduction of a compound of formula:

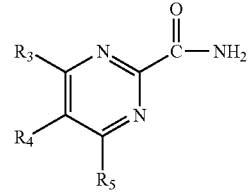

(XII)

in which $R_3$, $R_4$ and $R_5$ are as defined for a compound of formula (I). Reduction is effected by means of a reducing agent such as borane in a solvent such as tetrahydrofuran, at a temperature between room temperature and the reflux temperature of the solvent, followed by acid hydrolysis.

Finally, according to another variant, a compound of formula (II) in which $R_2$=H can also be prepared by reaction of a compound of formula:

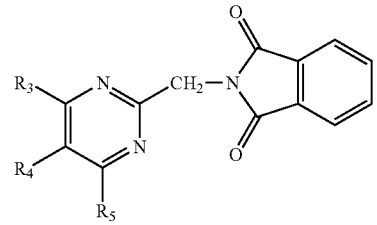

(XXI)

in which $R_3$, $R_4$ and $R_5$ are as defined for a compound of formula (I), with hydrazine hydrate, in a solvent such as methanol and at a temperature between room temperature and the reflux temperature of the solvent.

The compounds of formula (III) are known.

The compounds of formula (IV) are commercially available or are described in the literature, or can be prepared by methods that are described in the literature, such as in J. Org. Chem. USSR, 1970, 6, 2454-2458; J. Am. Chem. Soc., 1952, 74, 2008; J. Med. Chem., 1977, 20 (10) 1235-1239; EP 0 469 984; WO 95/18105.

For example, the compounds of formula (IV) can be prepared by halogenation of the corresponding sulfonic acids or their salts, for example their sodium or potassium salts. The reaction is carried out in the presence of a halogenating agent such as phosphorus oxychloride, thionyl chloride, phosphorus trichloride, phosphorus tribromide or phosphorus pentachloride, without solvent or in a solvent such as a halogenated hydrocarbon or N,N-dimethylformamide and at a temperature between −10° C. and 200° C.

The compounds of formulae (V), (VII), (VIII) and (IX) are known or are prepared by known methods.

The compounds of formula (X) are prepared from compounds of formula:

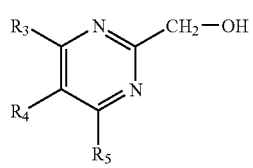

(XIII)

in which $R_3$, $R_4$ and $R_5$ are as defined for a compound of formula (I), by classical methods mentioned previously.

Thus, for example, for a compound of formula (X), when Y represents a halogen atom, a compound of formula (XIII) is treated with a halogenating agent such as $PCl_5$, $PBr_3$, HBr or $BBr_3$, in a solvent such as dichloromethane and at a temperature between 0° C. and room temperature.

When, in a compound of formula (X), Y represents a methanesulfonate, a benzenesulfonate, a p-toluenesulfonate or a trifluoromethanesulfonate, a compound of formula (XIII) is reacted with a sulfonyl chloride of formula $W-SO_2-Cl$ in which W represents a methyl, a phenyl, a p-tolyl or a trifluoromethyl. The reaction is carried out in the presence of a base such as triethylamine, pyridine or N,N-diisopropylethylamine, in a solvent such as dichloromethane or toluene and at a temperature between −20° C. and the reflux temperature of the solvent.

The compounds of formula (X) in which $R_3$=H can also be prepared by reaction of a compound of formula:

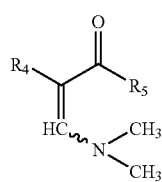

(XIV)

in which $R_4$ and $R_5$ are as defined for a compound of formula (I), with chloroacetamidine hydrochloride in a solvent such as EtOH or MeOH in the presence of a base such as sodium methylate, and at a temperature between 0° C. and room temperature.

The compounds of formula (XI) are known.

The compounds of formula (XII) are prepared by reaction of an acid or a functional derivative of that acid of formula:

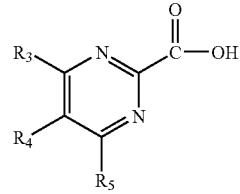

(XV)

in which $R_3$, $R_4$ and $R_5$ are as defined for a compound of formula (I), with ammonia according to the methods previously mentioned for the reaction of a compound (II) with a compound (III).

The compounds of formula (XIII) are prepared by the methods described in WO 2004/110453 and as illustrated in the following reaction scheme.

SCHEME 1

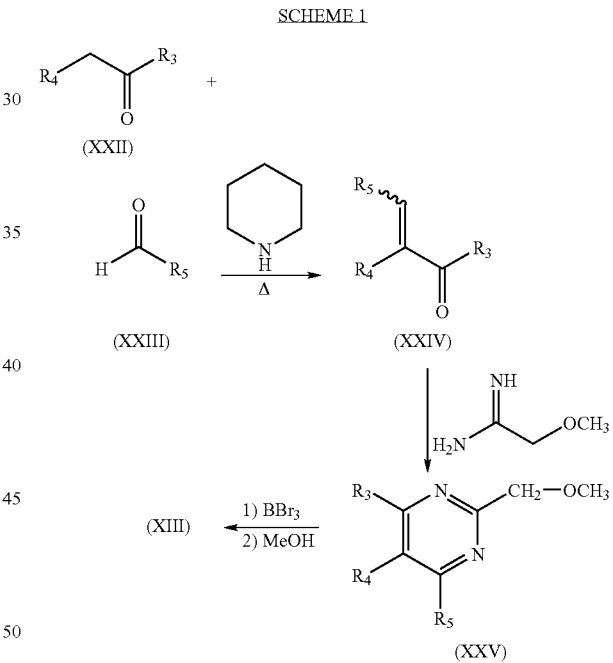

The compounds of formula (XIII) can also be prepared by reduction of the compounds of formula:

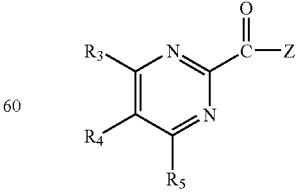

(XVI)

in which $R_3$, $R_4$ and $R_5$ are as defined for a compound of formula (I) and Z represents a ($C_1$-$C_2$)-alkoxy.

The reaction is carried out in the presence of a reducing agent such as sodium borohydride or aluminum and lithium hydride, in a solvent such as tetrahydrofuran, and at a temperature between −20° C. and room temperature.

The compounds of formula (XIV) are prepared by reaction of a compound of formula:

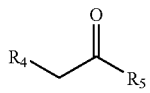

(XVII)

in which $R_4$ and $R_5$ are as defined for a compound of formula (I) with N,N-dimethylformamide dimethylacetal, in a solvent such as tetrahydrofuran and at a temperature between room temperature and the reflux temperature of the solvent.

The compounds of formula (XV) are prepared by the methods described in WO 2004/110453.

The compounds of formula (XV) in which $R_3$=H can be prepared by oxidation of the compounds of formula:

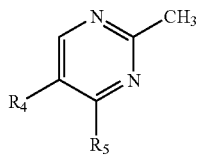

(XVIII)

in which $R_4$ and $R_5$ are as defined for a compound of formula (I) in the presence of an oxidizing agent such as selenium dioxide, in a solvent such as pyridine and at a temperature between room temperature and the reflux temperature of the solvent.

The compounds of formula (XVI) are prepared by a reaction of esterification of the compounds of formula (XV) according to classical methods.

The compounds of formula (XVII) are prepared by reaction of a compound of formula $R_4$—$CH_2$—COOH (XIX) with a compound of formula $R_5$—COOMe (XX), in the presence of an alkali metal salt of hexamethyldisilazane such as the sodium salt for example, in a solvent such as tetrahydrofuran and at a temperature between −70° C. and 0° C.

The compounds of formula (XVIII) are prepared by reaction of a compound of formula (XIV) with acetamidine hydrochloride, in the presence of a base such as sodium methylate, in a solvent such as ethanol or methanol and at a temperature between room temperature and the reflux temperature of the solvent.

The compounds of formula (XIX) and (XX) are known or are prepared by known methods.

The compounds of formula (XXI) are prepared by reaction of a compound of formula (XIII) with phthalimide, in the presence of triphenylphosphine and diethylazo dicarboxylate, in a solvent such as tetrahydrofuran and at a temperature between −20° C. and room temperature.

The compounds of formulae (XXII) and (XXIII) are known or are prepared by known methods.

The following EXAMPLES describe the preparation of some compounds according to the invention. These examples are not limiting and are only intended to illustrate the present invention. The numbers of the example compounds refer to those given in TABLE X below, which shows the chemical structures and the physical properties of some compounds according to the invention.

The following abbreviations are used in the Preparations and in the Examples:
ether: diethyl ether
iso ether: diisopropyl ether
DMSO: dimethylsulfoxide
DMF: N,N-dimethylformamide
THF: tetrahydrofuran
PyBOP: benzotriazol-1-yloxytris(pyrrolidino)phosphonium hexafluorophosphate
TBTU: 2-(1H-benzotriazol-1-yl)-1,1,3,3-tetramethyluronium tetrafluoroborate
DCM: dichloromethane
AcOEt: ethyl acetate
DIPEA: diisopropylethylamine
DBU: 1,8-diazabicyclo[5.4.0]undec-7-ene
TFA: trifluoroacetic acid
2N hydrochloric ether: solution of 2N hydrochloric acid in diethyl ether
m.p.: melting point
RT: room temperature
b.p.: boiling point
HPLC: high-performance liquid chromatography
Silica H: silica gel 60 H marketed by Merck (Darmstadt)
Buffer solution pH=2: solution of 16.66 g of $KHSO_4$ and 32.32 g of $K_2SO_4$ in 1 liter of water.

The proton nuclear magnetic resonance ($^1$H-NMR) spectra are recorded at 200 MHz in DMSO-$d_6$. The chemical shifts δ are expressed in parts per million (ppm). The following abbreviations are used for interpreting the spectra: s: singlet, d: doublet, t: triplet, q: quadruplet, m: massive, mt: multiplet, bs: broad singlet, dd: doublet of doublets.

The compounds of the invention are analyzed by a combination of LC/UV/MS (liquid chromatography/UV detection/mass spectrometry). The molecular peak (MH$^+$) and the retention time (tr) in minutes, are measured.

Method 1:

Column used: Symmetry C18 of 2.1×50 mm, 3.5 μm, at 30° C., flow rate 0.4 ml/min.
The eluent has the following composition:
solvent A: 0.005% of trifluoroacetic acid (TFA) in water at pH 3.15;
solvent B: 0.005% of TFA in acetonitrile.

Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

UV detection is carried out at λ=210 nm and detection of mass in positive ESI chemical ionization mode in order to observe the ions from protonation of the compounds analyzed (MH$^+$).

Method 2:

Column used: XTerra MS C18 of 2.1×30 mm, 3.5 μm, at 30° C., flow rate 0.8 ml/min.
The eluent has the following composition:
solvent A: 0.025% TFA in water;
solvent B: 0.025% TFA in acetonitrile.

Gradient:

| Time (min) | % A | % B |
|---|---|---|
| 0 | 100 | 0 |
| 2 | 0 | 100 |
| 2.7 | 0 | 100 |
| 2.75 | 100 | 0 |

UV detection is effected with a diode-array detector between 210 and 400 nm and detection of mass in positive ESI chemical ionization mode.

Preparations

1. Preparations of the Compounds of Formula (XVII) Preparation 1.1

2-(4-Bromophenyl)-1-(2,4-dichlorophenyl)ethanone (XVII):

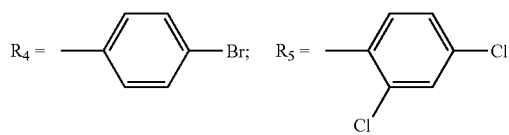

436 ml of a 2M solution of the sodium salt of hexamethyldisilazane in THF is cooled to −60° C., in a nitrogen atmosphere, 400 ml of THF is added then, dropwise, a solution of 75 g of 4-bromophenylacetic acid in 100 ml of THF and it is stirred for 1 h 30 min at −70° C. Then 67.9 g of methyl-2,4-dichlorobenzoate is added dropwise, stirred for 30 minutes, then the temperature is allowed to rise to 5° C. The reaction mixture is poured onto a mixture of ice/1 liter of 2N HCl, extracted with ether, the organic phase is washed with a saturated NaHCO$_3$ solution, then with water, dried over Na$_2$SO$_4$ and the solvent is evaporated under vacuum to a volume of 200 ml, pentane is added and the crystalline product that forms is dried. 80 g of the expected compound is obtained.

Following the procedure described in Preparation 1.1, the compounds of formula (XVII) shown in TABLE I below are prepared:

TABLE I

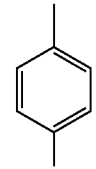

TABLE I-continued

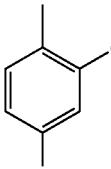

2. Preparations of the Compounds of Formula (XIV) Preparation 2.1

2-(4-Bromophenyl)-1-(2,4-dichlorophenyl)-3-(dimethylamino)prop-2-en-1-one (XIV):

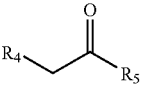

A mixture of 30 g of the compound from Preparation 1.1 and 31.2 g of N,N-dimethylformamide dimethylacetal in 100 ml of THF is heated under reflux for 3 hours. The reaction mixture is concentrated under vacuum, the residue is taken up in iso ether, stirred, the crystalline product that forms is dried and then washed with pentane. 32.98 g of the expected compound is obtained.

Following the procedure described in Preparation 2.1, the compounds of formula (XIV) shown in TABLE II below are prepared:

TABLE II

TABLE II-continued

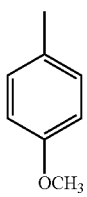

(XIV)

| Preparations | R4 | R5 |
|---|---|---|
| 2.3 | 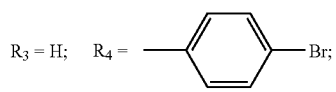 | 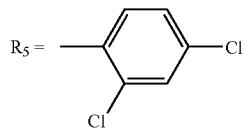 |

3. Preparations of the Compounds of Formula (X) Preparation 3.1

5-(4-Bromophenyl)-2-(chloromethyl)-4-(2,4-dichlorophenyl)pyrimidine (X):

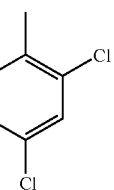

$R_3 = H$

A mixture of 17.6 g of the compound from preparation 2.1 and 8.5 g of chloroacetamidine hydrochloride in 100 ml EtOH is stirred for 10 minutes at RT, then 12.5 ml of a 30% solution of MeONa in MeOH is added and it is stirred for 2 hours at RT. Then 8.5 g of chloroacetamidine hydrochloride is added, it is stirred for 10 minutes at RT, then 12.5 ml of a 30% solution of MeONa in MeOH is added and it is stirred overnight at RT. The reaction mixture is poured into 500 ml of water/ice mixture, extracted with ether, the organic phase is washed with saturated NaCl solution, dried over MgSO₄ and the solvent is evaporated under vacuum. The residue is chromatographed on silica gel, eluting with heptane then with the gradient of heptane/AcOEt mixture from (99/1; v/v) to (80/20; v/v). 11.9 g of the expected compound is obtained.

Following the procedure described in Preparation 3.1, the compounds of formula (X) shown in TABLE III below are prepared:

TABLE III

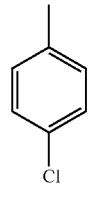

(X)

$R_3 = H$
$Y = Cl$

| Preparations | R4 | R5 |
|---|---|---|
| 3.2 | 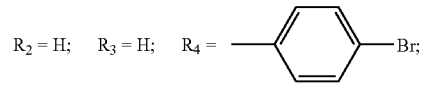 |  |
| 3.3 | 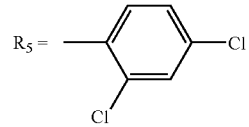 |  |

4. Preparations of the Compounds of Formula (II) Preparation 4.1

1-[5-(4-Bromophenyl)-4-(2,4-dichlorophenyl)pyrimidin-2-yl]methanamine hydrochloride (II):

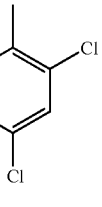

$R_2 = H$; $R_3 = H$;

A mixture of 11 g of the compound from Preparation 3.1, 4.35 g of hexamethylenetetramine and 4.03 g of sodium iodide in 220 ml of EtOH is stirred overnight at RT and then heated at 50° C. for 5 hours. Then 27 ml of a concentrated HCl solution is added and it is heated at 80° C. for 5 hours. After concentrating under vacuum, the residue is taken up in 2 liters of water, the aqueous phase is washed twice with ether, the aqueous phase is alkalized by adding concentrated NaOH solution, extracted with ether, the organic phase is washed with a saturated NaCl solution, dried over MgSO₄, filtered, the filtrate is acidified to pH=1 by adding 2N hydrochloric ether, and the precipitate that forms is dried and then washed with ether. 7.8 g of the expected compound is obtained.

Following the procedure described in Preparation 4.1, the compounds of formula (II) shown in TABLE IV below are prepared:

TABLE IV (II)

Structure: pyrimidine with CH₂—NH₂, HCl at position 2, R₄ at position 5, R₅ at position 4

R₂ = H
R₃ = H

| Preparations | R₄ | R₅ |
|---|---|---|
| 4.2 | 4-chlorophenyl | 2,4-dichlorophenyl |
| 4.3 | 4-methoxyphenyl (OCH₃) | 2,4-dichlorophenyl |

5. Preparations of the Compounds of Formula (XXIV) Preparation 5.1

3-(4-Bromophenyl)-4-(2,4-dichlorophenyl)but-3-en-2-one (XXIV):

$R_3 = $ —CH₃;   $R_4 = $ 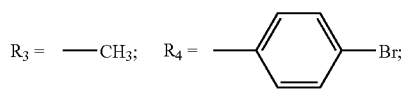

$R_5 = $ 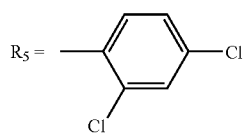

A mixture of 15.9 g of 1-(4-bromophenyl)acetone, 13 g of 2,4-dichlorobenzaldehyde and 0.5 g of piperidine in 300 ml of benzene is heated under reflux for 18 hours, removing the water that forms by means of a Dean Stark. 0.3 g of piperidine is added, and it is refluxed for a further 24 hours. The reaction mixture is concentrated under vacuum, obtaining 27 g of the expected compound in the form of oil.

Following the procedure described in Preparation 5.1, the compounds of formula (XXIV) shown in TABLE V below are prepared:

TABLE V (XXIV)

Structure: R₄–C(=O)–C(R₃)=CH–R₅ type enone

| Preparations | R₃ | R₄ | R₅ |
|---|---|---|---|
| 5.2 | —CH₃ | 4-methylphenyl | 2,4-dichlorophenyl |

6. Preparations of the Compounds of Formula (XXV) Preparation 6.1

5-(4-Bromophenyl)-4-(2,4-dichlorophenyl)-2-(methoxymethyl)-6-methyl pyrimidine (XXV):

$R_3 = $ —CH₃;   $R_4 = $ 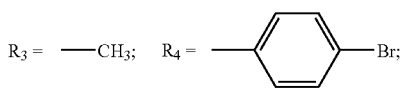

$R_5 = $ 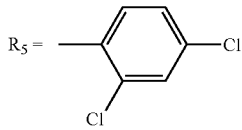

23 g of potassium tert-butylate is added to a mixture of 37 g of the compound from Preparation 5.1 and 25 g of 2-methoxyethanimidamide in 300 ml of DMSO, it is heated at 80° C. for 2 hours and then at 120° C. overnight. The solvent is concentrated under vacuum to a volume of 150 ml, the reaction mixture is poured onto 2 liters of ice water, extracted with ether, the organic phase is washed with water, then with saturated NaCl solution, dried over MgSO₄ and the solvent is evaporated under vacuum. The residue is chromatographed on silica gel, eluting with heptane and then with a gradient of heptane/AcOEt mixture up to (50/50; v/v). 6.4 g of the expected compound is obtained in the form of foam.

Following the procedure described in Preparation 6.1, the compounds of formula (XXV) shown in TABLE VI below are prepared:

TABLE VI

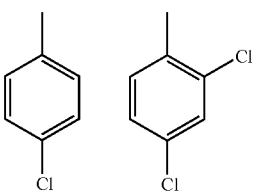
(XXV)

| Preparations | $R_3$ | $R_4$ | $R_5$ |
|---|---|---|---|
| 6.2 | —$CH_3$ |  | 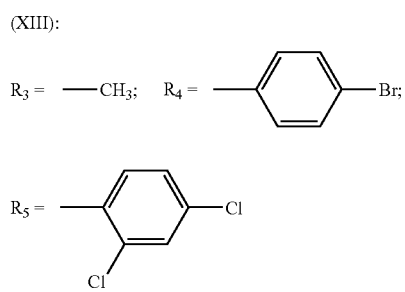 |

TABLE VII

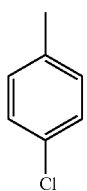
(XIII)

| Preparations | $R_3$ | $R_4$ | $R_5$ |
|---|---|---|---|
| 7.2 | —$CH_3$ | 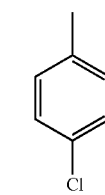 | 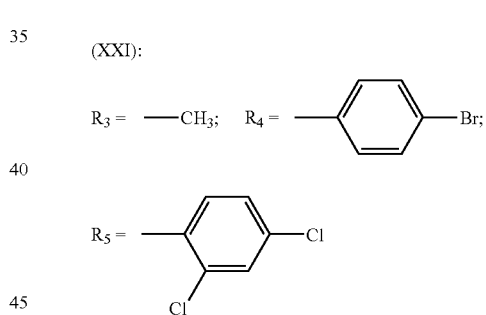 |

7. Preparations of the Compounds of Formula (XIII) Preparation 7.1

[5-(4-Bromophenyl)-4-(2,4-dichlorophenyl)-6-methylpyrimidin-2-yl]methanol (XIII):

$R_3 =$ —$CH_3$;  $R_4 =$ 4-Br-phenyl;

$R_5 =$ 2,4-dichlorophenyl

A solution of 6.4 g of the compound from Preparation 6.1 in 160 ml of DCM is cooled to −78° C., 24 ml of a 1M solution of boron tribromide in DCM is added dropwise, stirring and allowing the temperature to rise to 0° C., then stirring for one hour. The reaction mixture is cooled to −78° C., 65 ml of MeOH is added dropwise, stirring and allowing the temperature to rise to room temperature, and continuing stirring for 2 hours. The reaction mixture is concentrated under vacuum, the residue is taken up in MeOH and the solvent is evaporated under vacuum. The residue is taken up with 200 ml of MeOH, 16 ml of concentrated HCl is added, and it is concentrated under vacuum. The residue is extracted with AcOEt, the organic phase is washed with water, then with saturated NaCl solution, dried over $MgSO_4$, and the solvent is evaporated under vacuum. 6.1 g of the expected compound is obtained.

Following the procedure described in Preparation 7.1, the compounds of formula (XIII) shown in TABLE VII below are prepared:

8. Preparations of the Compounds of Formula (XXI) Preparation 8.1

2-[[5-(4-Bromophenyl)-4-(2,4-dichlorophenyl)-6-methylpyrimidin-2-yl]methyl]-1H-isoindole-1,3-(2H)-dione (XXI):

$R_3 =$ —$CH_3$;  $R_4 =$ 4-Br-phenyl;

$R_5 =$ 2,4-dichlorophenyl

A mixture of 6.1 g of the compound of Preparation 7.1, 2.33 g of phthalimide and 4.15 g of triphenylphosphine in 120 ml of THF is cooled to −10° C., 2.75 g of diethylazodicarboxylate is added dropwise, stirring and allowing the temperature to rise to room temperature, then stirring for 5 hours at RT. The reaction mixture is concentrated under vacuum, the residue is extracted with AcOEt, the organic phase is washed with buffer solution pH=2, with water, then with saturated $NaHCO_3$ solution, and with saturated NaCl solution, dried over $MgSO_4$, and the solvent is evaporated under vacuum. The residue is taken up in ether, stirred, and the crystalline product that forms is dried. 3.8 g of the expected compound is obtained.

Following the procedure described in Preparation 8.1, the compounds of formula (XXI) shown in TABLE VIII below are prepared:

TABLE VIII

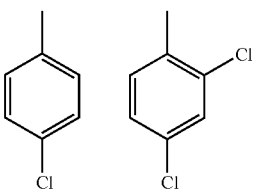

(XXI)

| Preparations | R₃ | R₄ | R₅ |
|---|---|---|---|
| 8.2 | —CH₃ | 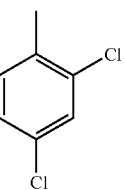 | |

9. Preparations of the Compounds of Formula (II) Preparation 9.1

1-[5-(4-Bromophenyl)-4-(2,4-dichlorophenyl)-6-methylpyrimidin-2-yl]methanamine hydrochloride (II):

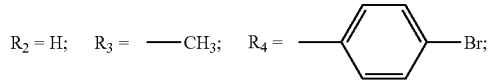

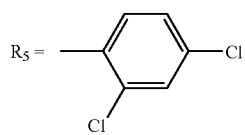

A mixture of 3.8 g of the compound from Preparation 8.1 and 0.7 ml of hydrazine hydrate in 70 ml of MeOH is heated under reflux for 2 hours 30 minutes. The reaction mixture is concentrated under vacuum, the residue is extracted with ether, the organic phase is washed with 1N NaOH solution, with saturated NaHCO₃ solution, with saturated NaCl solution, then dried over MgSO₄, acidified to pH=1 by adding 2N hydrochloric ether, stirred, and the crystalline product that forms is dried. 2.9 g of the expected compound is obtained.

Following the procedure described in Preparation 9.1, the compounds of formula (II) shown in TABLE IX below are prepared:

TABLE IX

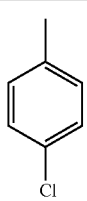

(II)

| Preparations | R₃ | R₄ | R₅ |
|---|---|---|---|
| 9.2 | —CH₃ | 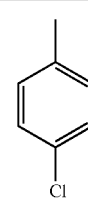 | |

EXAMPLE 1

Compound No. 1

N-[[5-(4-Bromophenyl)-4-(2,4-dichlorophenyl)pyrimidin-2-yl]methyl]-2-propyl pentanamide A mixture of 0.5 g of the compound from Preparation 4.1, 0.17 g of 2-propylpentanoic acid, 0.55 ml of triethylamine and 0.7 g of PyBOP in 10 ml of DCM is stirred overnight at RT. It is concentrated under vacuum, extracted with AcOEt, the organic phase is washed with 1N HCl solution, with water, then with saturated NaHCO₃ solution, dried over MgSO₄, and the solvent is evaporated under vacuum. The residue is taken up in EtOH 95, the crystalline product that forms is dried and then washed with pentane. 0.285 g of the expected compound is obtained.

MH⁺=534; tr=11.75 (method 1)

EXAMPLE 2

Compound No. 5

N-[[5-(4-Bromophenyl)-4-(2,4-dichlorophenyl)pyrimidin-2-yl]methyl-3-chlorobenzenesulphonamide A mixture of 0.5 g of the compound from Preparation 4.1, 0.25 g of 3-chlorobenzenesulphonyl chloride and 0.39 ml of triethylamine in 10 ml of DCM is stirred for 2 hours at RT. The reaction mixture is washed with 1N HCl solution, with water, then with saturated NaHCO₃ solution, dried over MgSO₄, and the solvent is evaporated under vacuum. The residue is taken up in EtOH and the crystalline product that forms is dried. 0.44 g of the expected compound is obtained.

MH⁺=582; tr=11.44 (method 1)

EXAMPLE 3

Compound No. 13

N-[[5-(4-Chlorophenyl)-4-(2,4-dichlorophenyl)pyrimidin-2-yl]methyl]cycloheptanecarboxamide A mixture of 0.5 g of the compound from Preparation 4.2, 0.18 g of cycloheptanecarboxylic acid, 0.52 ml of triethylamine and 0.77 g of PyBOP in 10 ml of DCM is stirred for 1 hour at RT. The reaction mixture is washed with 1N HCl solution, with water, and with a saturated $NaHCO_3$ solution, dried over $MgSO_4$, and the solvent is evaporated under vacuum. The residue is chromatographed on silica gel, eluting with heptane and then with the gradient of heptane/AcOEt mixture from (99/1; v/v) to (50/50; v/v). 0.39 g of the expected compound is obtained.

$MH^+$=488; tr=11.34 (method 1)

EXAMPLE 4

Compound No. 33

N-[[5-(4-Chlorophenyl)-4-(2,4-dichlorophenyl)pyrimidin-2-yl]methyl]-N'-[3-(trifluoromethyl)phenyl]urea A mixture of 0.5 g of the compound from Preparation 4.2 (free base) and 0.24 g of 3-(trifluoromethyl)phenyl isocyanate in 5 ml of DCM is stirred overnight at RT. It is concentrated under vacuum and the residue is chromatographed on silica gel, eluting with heptane and then with the gradient of heptane/AcOEt mixture from (99/1; v/v) to (50/50; v/v). The product obtained is taken up in pentane and the precipitate that forms is dried. 0.51 g of the expected compound is obtained.

$MH^+$=551; tr=11.54 (method 1)

EXAMPLE 5

Compound No. 40

N-[[4-(2,4-Dichlorophenyl)-5-(4-methoxyphenyl)pyrimidin-2-yl]methyl]-4-phenoxybenzamide A mixture of 0.4 g of the compound from Preparation 4.3, 0.22 g of 4-phenoxybenzoic acid, 0.4 ml of triethylamine and 0.63 g of PyBOP in 10 ml of DCM is stirred overnight at RT. It is concentrated under vacuum, the residue is extracted with ether, the organic phase is washed with water, with 1N HCl solution, with water, and then with saturated $NaHCO_3$ solution, it is dried over $MgSO_4$ and the solvent is evaporated under vacuum to a residual volume of 5 ml. It is stirred, and the crystalline product that forms is dried. 0.32 g of the expected compound is obtained after crystallization in EtOH.

$MH^+$=556; tr=11.19 (method 1)

EXAMPLE 6

Compound No. 55

N-[[5-(4-Bromophenyl)-4-(2,4-dichlorophenyl)-6-methylpyrimidin-2-yl]methyl]-3,3-diphenylpropanamide A mixture of 0.4 g of the compound from Preparation 9.1, 0.2 g of 3,3-diphenylpropanoic acid, 0.3 ml of triethylamine and 0.55 g of PyBOP in 10 ml of DCM is stirred overnight at RT. It is concentrated under vacuum, the residue is extracted with ether, the organic phase is washed with water, with 1N HCl solution, with water, and then with saturated $NaHCO_3$ solution, dried over $MgSO_4$, and the solvent is evaporated under vacuum. The residue is chromatographed on silica gel, eluting with heptane and then with the gradient of heptane/AcOEt mixture to (50/50; v/v). 0.3 g of the expected compound is obtained after crystallization in EtOH.

$MH^+$=630; tr=11.98 (method 1)

EXAMPLE 7

Compound No. 56

N-[[5-(4-Bromophenyl)-4-(2,4-dichlorophenyl)-6-methylpyrimidin-2-yl]methyl]-3-(trifluoromethyl)benzenesulfonamide 0.24 g of 3-(trifluoromethyl)benzenesulfonyl chloride is added to a mixture of 0.4 g of the compound from Preparation 9.1 and 0.3 ml of triethylamine in 10 ml of DCM, and it is stirred for 15 minutes at RT. The reaction mixture is washed with 1N HCl solution, with water, and then with saturated $NaHCO_3$ solution, it is dried over $MgSO_4$, and the solvent is evaporated under vacuum. The residue is taken up in EtOH, stirred, and the crystalline product that forms is dried, washed with EtOH and then with pentane. 0.37 g of the expected compound is obtained.

$MH^+$=630; tr=11.96 (method 1)

EXAMPLE 8

Compound No. 60

4-tert-Butyl-N-[[5-(4-chlorophenyl)-4-(2,4-dichlorophenyl)-6-methylpyrimidin-2-yl]methyl]benzamide A mixture of 0.4 g of the compound from Preparation 9.2, 0.18 g of 4-tert-butylbenzoic acid, 0.4 ml of triethylamine and 0.6 g of PyBOP in 10 ml of DCM is stirred overnight at RT. The reaction mixture is concentrated under vacuum, the residue is extracted with ether, the organic phase is washed with water, with 1N HCl solution, with water, and then with saturated $NaHCO_3$ solution, it is dried over $MgSO_4$, and the solvent is evaporated under vacuum. The residue is taken up in a minimum of ether, iso ether is added, it is stirred, and the crystalline product that forms is dried and then washed with iso ether. 0.35 g of the expected compound is obtained.

$MH^+$=538; tr=12.27 (method 1)

The following table shows the chemical structures and the physical properties of some examples of compounds according to the invention.

TABLE X (I)

Structure: Pyrimidine with R3 at position 4, R4 at position 5, R5 at position 6, and at position 2: —CH2—N(R2)—X—R1

| Compounds No. | —X— | R1 | R2 | R3 | R4 | R5 | MH+; tr (min) (method) crystallization solvent |
|---|---|---|---|---|---|---|---|
| 1 | —CO— | —CH(CH2—CH2CH3)2 | H | H | 4-Br-phenyl | 2,4-diCl-phenyl | 534; 11.75 (method 1) EtOH 95 |
| 2 | —CO— | 4-Cl-phenyl | H | H | 4-Br-phenyl | 2,4-diCl-phenyl | 546; 10.60 (method 1) EtOH |
| 3 | —CO— | 4-C(CH3)3-phenyl | H | H | 4-Br-phenyl | 2,4-diCl-phenyl | 568; 11.59 (method 1) iso ether |
| 4 | —CO— | 4-CF3-phenyl | H | H | 4-Br-phenyl | 2,4-diCl-phenyl | 580; 10.99 (method 1) iso ether/ pentane |
| 5 | —SO2— | 3-Cl-phenyl | H | H | 4-Br-phenyl | 2,4-diCl-phenyl | 582; 11.44 (method 1) EtOH |
| 6 | —SO2— | 4-Cl-phenyl | H | H | 4-Br-phenyl | 2,4-diCl-phenyl | 582; 11.53 (method 1) EtOH |

TABLE X-continued (I)

*Structure: Pyrimidine ring with R3, R4, R5 substituents and CH2-N(R2)-X-R1 side chain*

| Compounds No. | —X— | R1 | R2 | R3 | R4 | R5 | MH+; tr (min) (method) crystallization solvent |
|---|---|---|---|---|---|---|---|
| 7 | —SO2— | 3-methoxyphenyl | H | H | 4-bromophenyl | 2,4-dichlorophenyl | 578; 10.36 (method 1) EtOH |
| 8 | —SO2— | 3-trifluoromethylphenyl | H | H | 4-bromophenyl | 2,4-dichlorophenyl | 616; 11.65 (method 1) EtOH NMR |
| 9 | —SO2— | 4-trifluoromethylphenyl | H | H | 4-bromophenyl | 2,4-dichlorophenyl | 616; 11.62 (method 1) EtOH NMR |
| 10 | —CO— | —CH(CH2CH3)2 | H | H | 4-chlorophenyl | 2,4-dichlorophenyl | 462.6; 1.91 (method 2) |
| 11 | —CO— | —CH(CH2—CH2CH3)2 | H | H | 4-chlorophenyl | 2,4-dichlorophenyl | 490.7; 2.02 (method 2) |
| 12 | —CO— | cyclopentyl | H | H | 4-chlorophenyl | 2,4-dichlorophenyl | 460.6; 1.89 (method 2) |

TABLE X-continued (I)

| Compounds No. | —X— | R₁ | R₂ | R₃ | R₄ | R₅ | MH+; tr (min) (method) crystallization solvent |
|---|---|---|---|---|---|---|---|
| 13 | —CO— | cycloheptyl-methyl | H | H | 4-chlorophenyl | 2,4-dichlorophenyl | 488; 11.34 (method 1) |
| 14 | —CO— | cyclohexyl-methyl | H | H | 4-chlorophenyl | 2,4-dichlorophenyl | 474.6; 1.94 (method 2) |
| 15 | —CO— | norbornyl (+,−) endo | H | H | 4-chlorophenyl | 2,4-dichlorophenyl | 486.6; 1.97 (method 2) |
| 16 | —CO— | 4-tert-butylphenyl-methyl, C(CH₃)₃ | H | H | 4-chlorophenyl | 2,4-dichlorophenyl | 524; 12.04 (method 1) |
| 17 | —CO— | 4-(trifluoromethyl)phenyl-methyl, CF₃ | H | H | 4-chlorophenyl | 2,4-dichlorophenyl | 536; 11.41 (method 1) NMR |
| 18 | —CO— | 4-phenoxyphenyl-methyl | H | H | 4-chlorophenyl | 2,4-dichlorophenyl | 560.6; 2.04 (method 2) |

TABLE X-continued
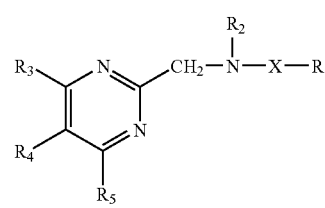
(I)
| Compounds No. | —X— | R₁ | R₂ | R₃ | R₄ | R₅ | MH+; tr (min) (method) crystallization solvent |
|---|---|---|---|---|---|---|---|
| 19 | —CO— | 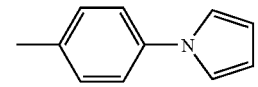 | H | H | 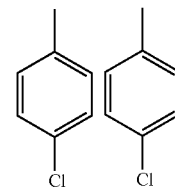 | 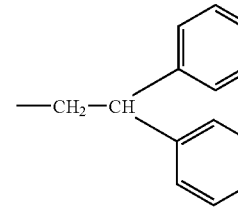 | 533.6; 1.99 (method 2) |
| 20 | —CO— | 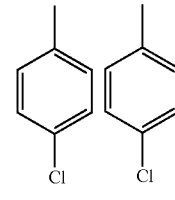 | H | H | 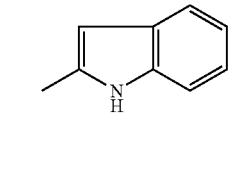 | 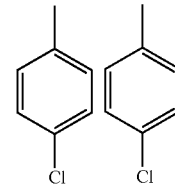 | 572.6; 2.01 (method 2) |
| 21 | —CO— | 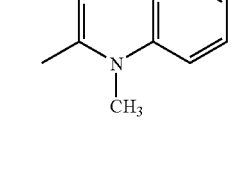 | H | H | 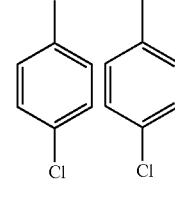 | 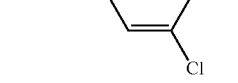 | 507; 10.93 (method 1) |
| 22 | —CO— | 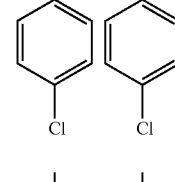 | H | H | 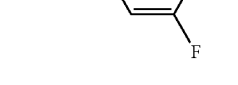 | 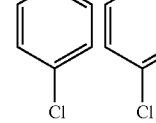 | 521.6; 2.01 (method 2) |
| 23 | —SO₂— |  | H | H |  |  | 538; 11.53 (method 1) |
| 24 | —SO₂— |  | H | H |  |  | 521.9; 2.15 (method 2) |

TABLE X-continued
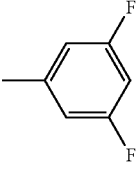
(I)
| Compounds No. | —X— | R₁ | R₂ | R₃ | R₄ | R₅ | MH+; tr (min) (method) crystallization solvent |
|---|---|---|---|---|---|---|---|
| 25 | —SO₂— | 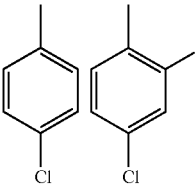 | H | H | 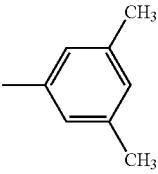 | 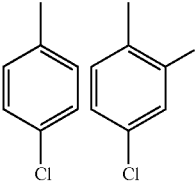 | 539.9; 2.18 (method 2) |
| 26 | —SO₂— | 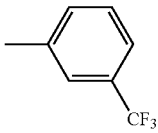 | H | H | 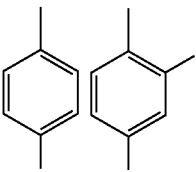 | 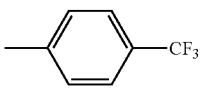 | 531.9; 2.22 (method 2) |
| 27 | —SO₂— | 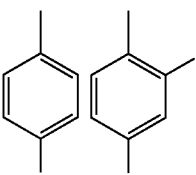 | H | H | 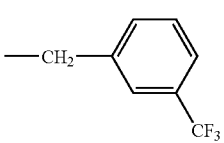 | 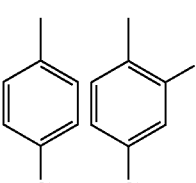 | 571.8; 2.21 (method 2) |
| 28 | —SO₂— | 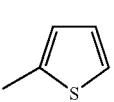 | H | H | 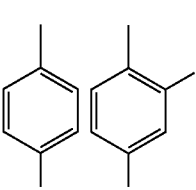 |  | 572; 11.69 (method 1) |
| 29 | —SO₂— |  | H | H |  |  | 586; 11.78 (method 1) |
| 30 | —SO₂— |  | H | H |  |  | 509.8; 2.12 (method 2) |

TABLE X-continued
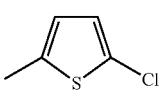
(I)
| Compounds No. | —X— | R₁ | R₂ | R₃ | R₄ | R₅ | MH+; tr (min) (method) crystallization solvent |
|---|---|---|---|---|---|---|---|
| 31 | —SO₂— | 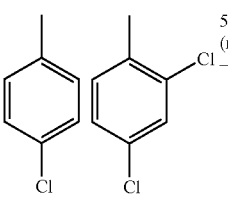 | H | H |  | 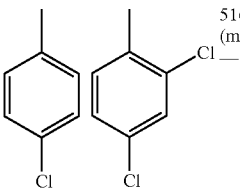 | 543.8; 2.22 (method 2) |
| 32 | —CONH— | 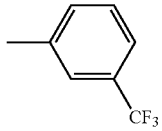 | H | H | 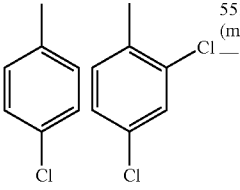 | 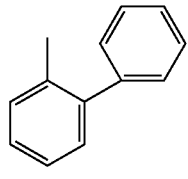 | 516.9; 2.16 (method 2) |
| 33 | —CONH— | 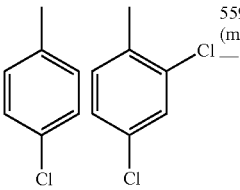 | H | H | 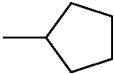 | 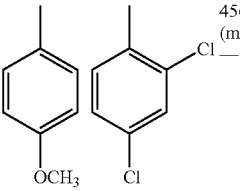 | 551; 11.54 (method 1) |
| 34 | —CONH— | 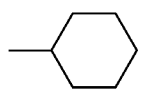 | H | H | 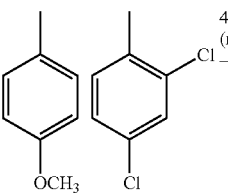 |  | 559; 11.55 (method 1) |
| 35 | —CO— |  | H | H |  |  | 456.7; 1.80 (method 2) |
| 36 | —CO— |  | H | H |  |  | 470.7; 1.85 (method 2) |

TABLE X-continued (I)

| Compounds No. | —X— | R₁ | R₂ | R₃ | R₄ | R₅ | MH+; tr (min) (method) crystallization solvent |
|---|---|---|---|---|---|---|---|
| 37 | —CO— | -C₆H₄-C(CH₃)₃ | H | H | 4-OCH₃-C₆H₄- | 2-Cl,4-Cl-C₆H₃- | 520.7; 2.01 (method 2) |
| 38 | —CO— | 3,5-(CH₃)₂-C₆H₃- | H | H | 4-OCH₃-C₆H₄- | 2-Cl,4-Cl-C₆H₃- | 492.7; 1.91 (method 2) |
| 39 | —CO— | 4-N(CH₂CH₃)₂-C₆H₄- | H | H | 4-OCH₃-C₆H₄- | 2-Cl,4-Cl-C₆H₃- | 535.7; 1.71 (method 2) |
| 40 | —CO— | 4-(O-C₆H₅)-C₆H₄- | H | H | 4-OCH₃-C₆H₄- | 2-Cl,4-Cl-C₆H₃- | 556.7; 1.96 (method 2) |
| 41 | —CO— | 4-(N-pyrrolyl)-C₆H₄- | H | H | 4-OCH₃-C₆H₄- | 2-Cl,4-Cl-C₆H₃- | 529.7; 1.91 (method 2) |
| 42 | —CO— | —CH₂—CH(C₆H₅)₂ | H | H | 4-OCH₃-C₆H₄- | 2-Cl,4-Cl-C₆H₃- | 568.7; 1.93 (method 2) |

TABLE X-continued
(I)
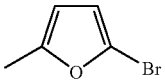
| Compounds No. | —X— | R₁ | R₂ | R₃ | R₄ | R₅ | MH+; tr (min) (method) crystallization solvent |
|---|---|---|---|---|---|---|---|
| 43 | —CO— | 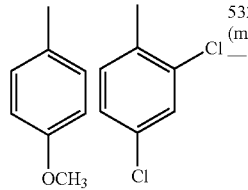 | H | H | 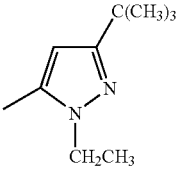 | 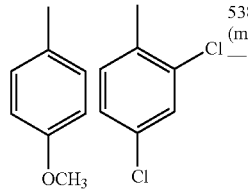 | 532.5; 1.85 (method 2) |
| 44 | —CO— | 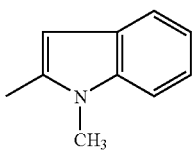 | H | H | 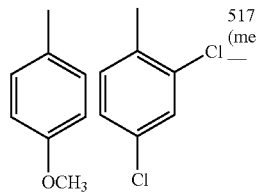 | 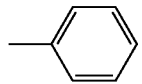 | 538.7; 1.94 (method 2) |
| 45 | —CO— | 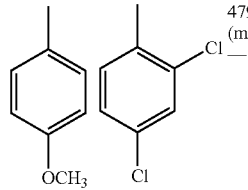 | H | H | 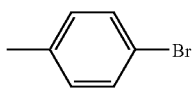 | 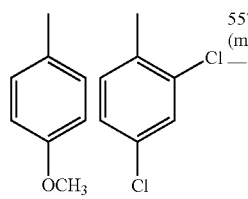 | 517.7; 1.93 (method 2) |
| 46 | —CONH— |  | H | H | 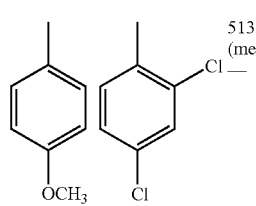 |  | 479.6; 1.79 (method 2) |
| 47 | —CONH— |  | H | H |  |  | 557.5; 1.90 (method 2) |
| 48 | —CONH— |  | H | H |  |  | 513.5; 1.88 (method 2) |

TABLE X-continued
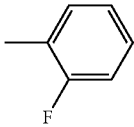
(I)
| Compounds No. | —X— | R₁ | R₂ | R₃ | R₄ | R₅ | MH+; tr (min) (method) crystallization solvent |
|---|---|---|---|---|---|---|---|
| 49 | —CONH— | 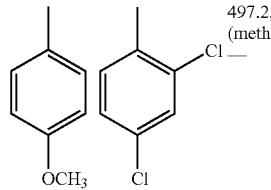 | H | H | 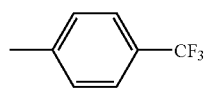 | 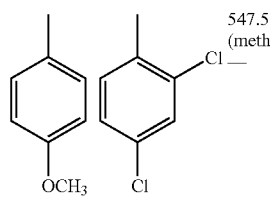 | 497.2; 1.82 (method 2) |
| 50 | —CONH— | 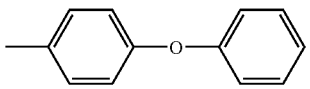 | H | H | 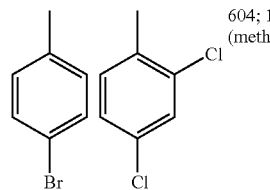 | 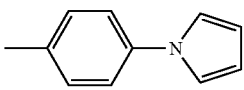 | 547.5; 1.92 (method 2) |
| 51 | —CO— | 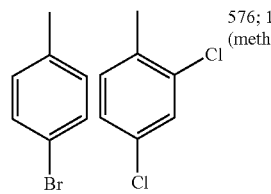 | H | H | 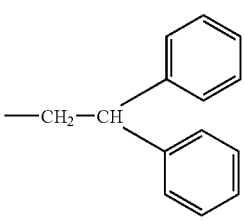 | 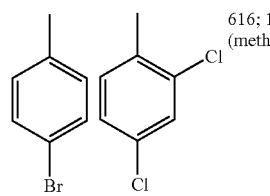 | 604; 11.83 (method 1) |
| 52 | —CO— | 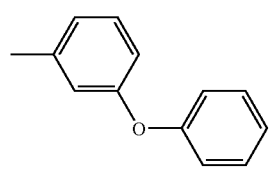 | H | H | 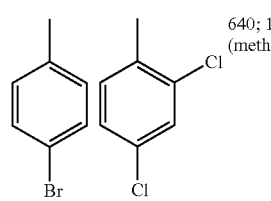 |  | 576; 11.32 (method 1) |
| 53 | —CO— |  | H | H |  |  | 616; 11.73 (method 1) |
| 54 | —SO₂— |  | H | H |  |  | 640; 19.57 (method 1) |

TABLE X-continued
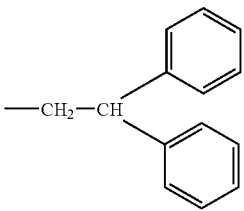
(I)
| Compounds No. | —X— | R₁ | R₂ | R₃ | R₄ | R₅ | MH+; tr (min) (method) crystallization solvent |
|---|---|---|---|---|---|---|---|
| 55 | —CO— | 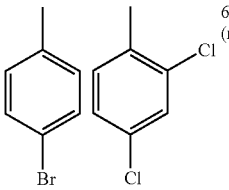 | H | —CH₃ | 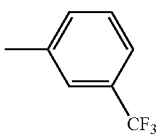 | 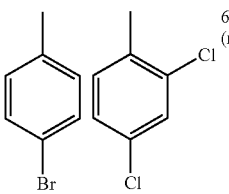 | 630; 11.98 (method 1) |
| 56 | —SO₂— | 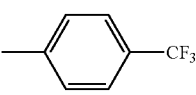 | H | —CH₃ | 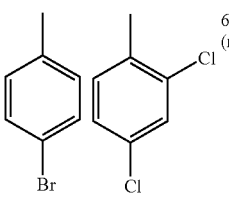 | 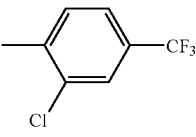 | 630; 11.96 (method 1) |
| 57 | —SO₂— | 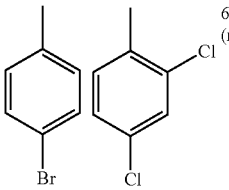 | H | —CH₃ | 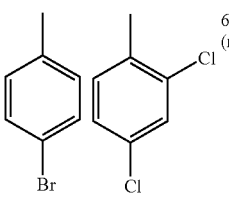 | 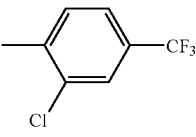 | 630; 11.59 (method 1) |
| 58 | —SO₂— | 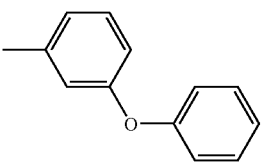 | H | —CH₃ | 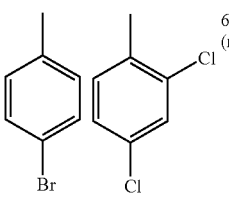 | 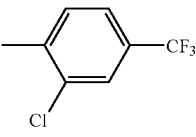 | 664; 12.31 (method 1) |
| 59 | —SO₂— | 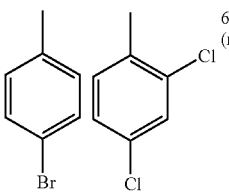 | H | —CH₃ | 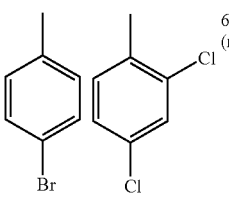 | 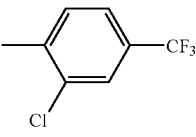 | 654; 19.93 (method 1) |
| 60 | —CO— | 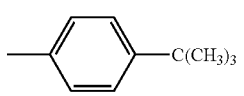 | H | —CH₃ | 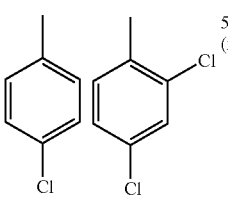 | 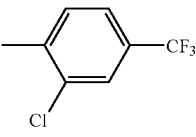 | 538; 12.27 (method 1) |

TABLE X-continued (I)

R3, R4, R5 substituted pyrimidine with CH2-N(R2)-X-R1 at 2-position

| Compounds No. | —X— | R₁ | R₂ | R₃ | R₄ | R₅ | MH+; tr (min) (method) crystallization solvent |
|---|---|---|---|---|---|---|---|
| 61 | —CO— | 4-CF₃-phenyl | H | —CH₃ | 4-Cl-phenyl | 2,4-diCl-phenyl | 550; 11.54 (method 1) |
| 62 | —SO₂— | 3-Cl-phenyl | H | —CH₃ | 4-Cl-phenyl | 2,4-diCl-phenyl | 552; 11.61 (method 1) |
| 63 | —SO₂— | 3-CF₃-phenyl | H | —CH₃ | 4-Cl-phenyl | 2,4-diCl-phenyl | 586; 11.77 (method 1) |
| 64 | —SO₂— | 4-CF₃-phenyl | H | —CH₃ | 4-Cl-phenyl | 2,4-diCl-phenyl | 586; 11.80 (method 1) |
| 65 | —SO₂— | 3-Cl-4-CF₃-phenyl | H | H | 4-Br-phenyl | 2,4-diCl-phenyl | 650; 12.48 (method 1) |
| 66 | —SO₂— | 2-NO₂-4-CF₃-phenyl | H | H | 4-Br-phenyl | 2,4-diCl-phenyl | 661; 11.18 (method 1) |

TABLE X-continued (I)

R3, R4, R5 substituted pyrimidine with -CH2-N(R2)-X-R1 group at position 2.

| Compounds No. | —X— | R1 | R2 | R3 | R4 | R5 | MH+; tr (min) (method) crystallization solvent |
|---|---|---|---|---|---|---|---|
| 67 | —SO2— | 3-Br-4-methyl-phenyl with CF3 | H | H | 4-Br-phenyl (methyl) | 3-Cl-4-Cl-phenyl (methyl) | 694; 12.38 (method 1) |
| 68 | —SO2— | 2-methyl-4-F-5-CF3-phenyl | H | H | 4-Br-phenyl (methyl) | 3-Cl-4-Cl-phenyl (methyl) | 634; 11.95 (method 1) |
| 69 | —SO2— | 4-F-3-CF3-phenyl | H | H | 4-Br-phenyl (methyl) | 3-Cl-4-Cl-phenyl (methyl) | 634; 12.06 (method 1) |
| 70 | —SO2— | 4-Cl-3-methyl-5-CF3-phenyl | H | H | 4-Br-phenyl (methyl) | 3-Cl-4-Cl-phenyl (methyl) | 650; 12.17 (method 1) |
| 71 | —SO2— | 4-OCHF2-phenyl | H | H | 4-Br-phenyl (methyl) | 3-Cl-4-Cl-phenyl (methyl) | 614; 11.43 (method 1) |

Compound No. 8: $^1$H-NMR: DMSO-d$_6$ (200 MHz): δ (ppm): 4.45: d: 2H; 7.05: d: 2H; 7.27-8.13: m: 9H; 8.67-8.85: m: 2H.

Compound No. 9: $^1$H-NMR: DMSO-d$_6$ (200 MHz): δ (ppm): 4.45: s: 2H; 7.06: d: 2H; 7.39: d: 1H; 7.45-7.63: m: 4H; 7.81: d: 2H; 7.93: d: 2H; 8.73: s: 1H; 8.77: s: 1H.

Compound No. 17: $^1$H-NMR: DMSO-d$_6$ (250 MHz): δ (ppm): 4.77: d: 2H; 7.21: d: 2H; 7.40: d: 2H; 7.44-7.54: m: 3H; 7.87: d: 2H; 8.11: d: 2H; 8.92: s: 1H; 9.41: t: 1H.

The compounds of formula (I) have very good affinity in vitro (IC$_{50}$≦5.10$^{-7}$ M) for the CB$_1$ cannabinoid receptors, in the experimental conditions described by M. Rinaldi-Carmona et al. (FEBS Letters, 1994, 350, 240-244).

The antagonistic character of the compounds of formula (I) was demonstrated by the results obtained in the models of adenylate-cyclase inhibition as described in M. Bouaboula et al., J. Biol. Chem., 1995, 270, 13973-13980, M. RinaldiCarmona et al., J. Pharmacol. Exp. Ther., 1996, 278, 871-878 and M. Bouaboula et al., J. Biol. Chem., 1997, 272, 22330-22339.

The interaction of a compound of formula (I) with the $CB_1$ receptors in the brain is determined in the mouse with the test of ex-vivo binding of [3H]-CP55940 after intravenous injection as described in M. Rinaldi-Carmona et al., FEBS Letters 1994, 350, 240-244 and M. Rinaldi-Carmona et al., Life Sciences 1995, 56, 1941-1947.

The interaction of a compound of formula (I) with the $CB_1$ receptors in the periphery is determined in the mouse with the test of reversal of the inhibitory effect of CP55940 on gastrointestinal transit after oral administration as described in M. Rinaldi-Carmona et al., JPET 2004, 310, 905-914.

The toxicity of the compounds of formula (I) is compatible with their use as medication.

Thus, according to another of its aspects, the invention relates to medicinal products for human or veterinary medicine which contain a compound of formula (I), or alternatively a solvate or a hydrate of the compound of formula (I).

Thus, the compounds according to the invention can be used in humans or in animals, in the treatment or prevention of diseases involving the $CB_1$ cannabinoid receptors, in human or in animals notably in mammals including non-limitatively dogs, cats, horses, cattle and sheep.

For example, and non-limitatively, the compounds of formula (I) can be used as psychotropic medicinal products, notably for the treatment of psychiatric disorders including anxiety, depression, mood disorders, insomnia, delusional disorders, obsessive disorders, psychoses in general, schizophrenia, attention deficit hyperactivity disorder (ADHD) in hyperactive children as well as for the treatment of disorders associated with the use of psychotropic substances, notably in the case of substance abuse and/or dependence on a substance, including alcohol addiction and nicotine addiction.

The compounds of formula (I) according to the invention can be used as medicinal products for the treatment of migraine, stress, diseases of psychosomatic origin, panic attacks, epilepsy, motor disorders, in particular dyskinesias or Parkinson's disease, tremor and dystonia.

The compounds of formula (I) according to the invention can also be used as medicinal products in the treatment of memory disorders, cognitive disorders, in particular in the treatment of senile dementias, of Alzheimer's disease, as well as in the treatment of attention or vigilance disorders. Moreover, the compounds of formula (I) can be used as neuroprotectors, in the treatment of ischaemia, head injuries and the treatment of acute or chronic neurodegenerative diseases: including chorea, Huntington chorea, Tourette syndrome.

The compounds of formula (I) according to the invention can be used as medicinal products in the treatment of pain: neuropathic pain, acute peripheral pain, chronic pain of inflammatory origin, pain induced by anticancer treatment.

The compounds of formula (I) according to the invention can be used as medicinal products in human or veterinary medicine in the treatment and prevention of disorders of appetite, craving (for sugars, carbohydrates, drugs, alcohols or any appetizing substance) and/or eating disorders, notably for the treatment and prevention of obesity or of bulimia as well as for the treatment of type II diabetes or non-insulin-dependent diabetes and for the treatment of dyslipidaemias, and of metabolic syndrome. Thus, the compounds of formula (I) according to the invention can be used in the treatment and prevention of obesity and of the risks associated with obesity, notably cardiovascular risks.

Moreover, the compounds of formula (I) according to the invention can be used as medicinal products in the treatment and prevention of gastrointestinal disorders, diarrhoea, ulcers, vomiting, bladder and urinary disorders, liver diseases such as chronic cirrhosis, fibrosis, hepatic steatosis, steatohepatitis, as well as disorders of endocrine origin, cardiovascular disorders, hypotension and atherosclerosis, haemorrhagic shock, septic shock, asthma, chronic bronchitis, chronic obstructive pulmonary diseases, Raynaud syndrome, glaucoma, fertility disorders, abortion, premature labor, inflammatory phenomena, immune system diseases, in particular autoimmune and neuroinflammatory such as rheumatoid arthritis, reactive arthritis, diseases resulting in demyelinization, multiple sclerosis, infectious and viral diseases such as encephalitis, cerebrovascular accidents and as medicinal products for anticancer chemotherapy, for the treatment of Guillain-Barré syndrome and for the treatment of bone diseases and osteoporosis.

According to the present invention, the compounds of formula (I) can be used quite particularly for the treatment of psychotic disorders, in particular schizophrenia, attention deficit hyperactivity disorders (ADHD) in hyperactive children; for the treatment of disorders of appetite and obesity; for the treatment of memory and cognitive disorders; for the treatment of alcohol dependence, nicotine dependence, i.e. for giving up drinking alcohol and smoking; acute or chronic neurodegenerative diseases.

More particularly, the compounds of formula (I) according to the present invention can be used in the treatment and prevention of disorders of appetite, metabolic disorders, gastrointestinal disorders, inflammatory phenomena, immune system diseases, psychotic disorders, alcohol dependence, and nicotine dependence.

According to one of its aspects, the present invention relates to the use of a compound of formula (I), and of its solvates or hydrates, for the treatment of the disorders and diseases stated above.

According to another of its aspects, the present invention relates to pharmaceutical compositions containing, as active principle, a compound according to the invention. These pharmaceutical compositions contain an effective dose of at least one compound according to the invention, a solvate or hydrate of said compound, as well as at least one pharmaceutically acceptable excipient.

Said excipients are selected depending on the pharmaceutical form and the desired method of administration, from the usual excipients that are known by a person skilled in the art.

The pharmaceutical compositions according to the present invention can contain, alongside a compound of formula (I), one or more other active principle(s) that can be used in the treatment of the disorders and diseases stated above.

Thus, the present invention also relates to pharmaceutical compositions containing a compound of formula (I) according to the present invention combined with one or more active principle(s) selected from one of the following therapeutic classes:

another antagonist of the $CB_1$ cannabinoid receptors;
    a modulator of the $CB_2$ cannabinoid receptors;
    an antagonist of the $AT_1$ angiotensin II receptors, alone or combined with a diuretic;
    an inhibitor of the converting enzyme, alone or combined with a diuretic or a calcium antagonist;
    a calcium antagonist;
    a diuretic;
    a beta-blocker alone or combined with a diuretic or a calcium antagonist;
    an antihyperlipaemic agent or an antihypercholesterolaemic agent;
    an antidiabetic agent;
    another anti-obesity agent or agent acting on metabolic disorders;
    a nicotinic agonist, a partial nicotinic agonist;

an antidepressant, an antipsychotic, an anxiolytic;
an anticancer agent or antiproliferative agent;
an opioid antagonist; as well as:
a memory-improving agent;
an agent for use in the treatment of alcoholism or of withdrawal symptoms;
an agent that can be used for treating osteoporosis;
a non-steroidal or steroidal anti-inflammatory drug;
an anti-infectious agent;
an analgesic;
an antiasthmatic agent.

"Antagonist of the $AT_1$ angiotensin II receptors" means a compound such as candesartan cilexetil, eprosartan, irbesartan, losartan potassium, olmesartan medoxomil, telmisartan, valsartan, and each of these compounds can itself be combined with a diuretic such as hydrochlorothiazide.

"Inhibitor of the converting enzyme" means a compound such as alacepril, benazepril, captopril, cilazapril, enalapril, enalaprilat, fosinopril, imidapril, lisinopril, moexipril, perindopril, quinapril, ramipril, spirapril, temocapril, trandolapril, zofenopril, and each of these compounds can itself be combined with a diuretic such as hydrochlorothiazide or indapamide or with a calcium antagonist such as amlodipine, diltiazem, felodipine or verapamil.

"Calcium antagonist" means a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline, verapamil.

"Beta-blocker" means a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertalol, tilisolol, timolol, xamoterol, xibenolol.

"Antihyperlipaemic or antihypercholesterolaemic agent" means a compound selected from the fibrates such as alufibrate, beclobrate, bezafibrate, ciprofibrate, clinofibrate, clofibrate, etofibrate, fenofibrate; the statins (HMG-CoA reductase inhibitors), such as atorvastatin, fluvastatin sodium, lovastatin, pravastatin, rosuvastatin, simvastatin, or a compound such as acipimox, aluminum nicotinate, azacosterol, cholestyramine, dextrothyroxine, meglutol, niceritrol, nicoclonate, nicotinic acid, beta-sitosterol, tiadenol.

"Antidiabetic agent" means a compound belonging to one of the following classes: sulfonylureas, biguanidines, alpha glucosidase inhibitors, thiazolidinediones, metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone, foliose, as well as insulin and insulin analogues.

"Other anti-obesity agent or agent acting on metabolic disorders" means a compound such as amfepramone, benfluorex, benzphetamine, indanorex, mazindol, mefenorex, methamphetamine, D-norpseudoephedrine, sibutramine, a lipase inhibitor (orlistat cetilistat), a PPAR agonist (peroxisome proliferator activated receptor agonist), a dopamine agonist, a leptin receptor agonist, a serotonin reuptake inhibitor, a beta-3 agonist, a CCK-A agonist, an NPY inhibitor, an MC4 receptor agonist, an MCH (melanin concentrating hormone) receptor antagonist, an orexin antagonist, a phosphodiesterase inhibitor, an inhibitor of 11βHSD (11-β-hydroxy steroid dehydrogenase), a DPP-IV (dipeptidyl peptidase IV) inhibitor, an antagonist (or inverse agonist) of histamine H3, a CNTF (ciliary neurotrophic factor) derivative, a GHS (growth hormone secretagogue) receptor agonist, a ghrelin modulator, an inhibitor of diacylglycerol acyltransferase (DGAT), a phosphodiesterase (PDE) inhibitor, a thyroid hormone agonist, a glucocorticoid receptor antagonist, an inhibitor of stearoyl-CoA-desaturase (SCD), a modulator of transporters of phosphate, of glucose, of fatty acid, of dicarboxylate, a $5HT_2$ antagonist, a $5HT_6$ antagonist, a bombesine agonist.

"Opioid antagonist" means a compound such as naltrexone, naloxone or nalmefene.

"Agent for use in the treatment of alcoholism as well as withdrawal symptoms" means acamprosate, the benzodiazepines, beta-blockers, clonidine, carbamazepine.

"Agent for use in the treatment of osteoporosis" means for example the bisphosphonates such as etidronate, clodronate, tiludronate, risedronate.

According to the present invention, it is also possible to combine other compounds having antihyperlipaemic, antihypercholesterolaemic, antidiabetic or anti-obesity properties. More particularly it is possible to combine compounds belonging to one of the following classes: inhibitors of PTP 1B (protein tyrosine phosphase-1B), VPAC-2 receptor agonists, GLK modulators, retinoid modulators, inhibitors of glycogen phosphorylase (HGLPa), glucagon antagonists, glucose-6-phosphate inhibitors, activators of pyruvate dehydrogenase kinase (PKD), modulators of RXR, FXR, LXR, inhibitors of SGLT (sodium-dependent glucose transporter), inhibitors of CETP (cholesteryl ester transfer protein), inhibitors of squalene synthetase, inhibitors of squalene epoxidase, inhibitors of triglyceride synthesis, inducers of LDL (low-density lipoprotein) receptors, inhibitors of IBAT, inhibitors of FBPase (fructose-1,6-biphosphatase), modulators of CART (cocaine-amphetamine-regulated transcript), MC4 (melanocortin 4) modulators, orexin receptor antagonists.

According to another aspect of the invention, the compound of formula (I), or one of its solvates or hydrates and the other combined active principle can be administered simultaneously, separately or spread over time.

"Simultaneous use" means administration of the compounds of the composition according to the invention contained in one single pharmaceutical form.

"Separate use" means administration, at the same time, of the two compounds of the composition according to the invention each contained in a separate pharmaceutical form.

"Use spread over time" means the successive administration, of the first compound of the composition of the invention, contained in one pharmaceutical form, then of the second compound of the composition according to the invention, contained in a separate pharmaceutical form. In this case, the period of time that passes between administration of the first compound of the composition according to the invention and administration of the second compound of the same composition according to the invention does not generally exceed 24 hours.

In the pharmaceutical compositions of the present invention for oral, sublingual, subcutaneous, intramuscular, intravenous, topical, local, intratracheal, intranasal, transdermal or rectal administration, the active principle of formula (I) above, or optionally its solvate or hydrate, can be administered in a unit form of administration, mixed with conventional pharmaceutical excipients, to animals and to human beings for the prophylaxis or treatment of the aforementioned disorders or diseases.

The appropriate unit forms of administration comprise the forms by the oral route such as tablets, soft or hard capsules, powders, granules and oral solutions or suspensions, forms for sublingual, buccal, intratracheal, intraocular, intranasal or inhalation administration, forms for topical, transdermal, subcutaneous, intramuscular or intravenous administration, forms for rectal administration, and implants. For topical application, the compounds according to the invention can be used in creams, gels, ointments or lotions.

As an example, a unit form of administration of a compound according to the invention in the form of a tablet can contain the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

By the oral route, the dose of active principle administered per day can reach 0.01 to 100 mg/kg, in one or more doses, preferably 0.02 to 50 mg/kg.

There may be special cases where higher or lower doses are appropriate; such doses are still within the scope of the invention. In accordance with usual practice, the dosage appropriate to each patient is determined by the doctor depending on the method of administration, and the weight and response of said patient.

According to another of its aspects, the present invention also relates to a method of treatment of the pathologies stated above that comprises the administration, to a patient, of an effective dose of a compound according to the invention, or hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

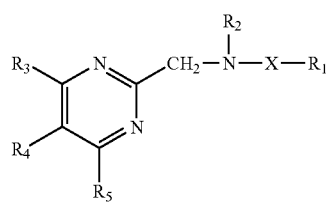

(I)

in which:
X represents a group

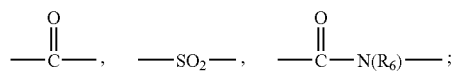

$R_1$ represents:
a $(C_1-C_{12})$-alkyl, unsubstituted or substituted one or more times with substituents selected independently from a fluorine atom, a hydroxyl, a $(C_1-C_4)$-alkoxy, a $(C_1-C_4)$-alkylthio, a phenoxy, a trifluoromethoxy radical, a difluoromethoxy radical, a difluoromethylthio radical or a trifluoromethylthio radical;

a non-aromatic $(C_3-C_{12})$-carbocyclic radical, unsubstituted or substituted one or more times with substituents selected independently from a $(C_1-C_4)$-alkyl, a $(C_1-C_4)$-alkoxy, a fluorine atom, a hydroxyl, a trifluoromethyl radical, a trifluoromethoxy radical or a $(C_1-C_4)$-alkylthio;

a $(C_3-C_7)$-cycloalkylmethyl, unsubstituted or substituted one or more times on the cycloalkyl with substituents selected independently from a $(C_1-C_4)$-alkyl, a $(C_1-C_4)$-alkoxy, a fluorine atom, a hydroxyl, a trifluoromethyl radical or a trifluoromethoxy radical;

a phenyl, unsubstituted or substituted one or more times with substituents selected independently from a halogen atom, a hydroxyl, an Alk group, an OAlk group, a methylenedioxy, a $(C_1-C_4)$-alkylamino, a di-$(C_1-C_4)$-alkylamino, a cyano, a nitro, an $S(O)_n$Alk group, an $OS(O)_n$Alk group, a $(C_1-C_4)$-alkylcarbonyl group; or from a phenyl, phenoxy, pyrrolyl, imidazolyl, pyridyl or pyrazolyl radical, said radical being unsubstituted or substituted one or more times with a $(C_1-C_4)$-alkyl;

a benzyl, unsubstituted or substituted one or more times on the phenyl with substituents selected independently from a halogen atom, an Alk group, a hydroxyl, an OAlk group, a methylenedioxy, an $S(O)_n$Alk group or an $OS(O)_n$Alk group and unsubstituted or substituted on alpha-methyl by one or two similar or dissimilar groups selected from a $(C_1-C_4)$-alkyl, a $(C_3-C_7)$-cycloalkyl;

a phenethyl, unsubstituted or substituted one or more times on the phenyl with substituents selected independently from a halogen atom, a $(C_1-C_4)$-alkyl, a $(C_1-C_4)$-alkoxy, a trifluoromethyl radical or a trifluoromethoxy radical;

a benzhydryl or a benzhydrylmethyl;

a 1,2,3,4-tetrahydronaphthalenyl, unsubstituted or substituted one or more times with a $(C_1-C_4)$-alkyl; or an aromatic heterocyclic radical selected from pyrrolyl, imidazolyl, furyl, thienyl, pyrazolyl, oxazolyl, pyridyl, indolyl, said radical being unsubstituted or substituted one or more times with substituents selected independently from a halogen atom, a $(C_1-C_4)$-alkyl, a $(C_1-C_4)$-alkoxy, a trifluoromethyl radical, a trifluoromethoxy radical, a cyano, a nitro or a $(C_1-C_4)$-alkylthio;

$R_2$ represents a hydrogen atom or a $(C_1-C_3)$-alkyl;

$R_3$ represents a hydrogen atom or a $(C_1-C_5)$-alkyl;

$R_4$ represents a phenyl, unsubstituted or substituted one or more times with substituents selected independently from a halogen atom, Alk group, OAlk group, $S(O)_n$Alk group or $OS(O)_n$Alk group;

$R_5$ represents a phenyl, unsubstituted or substituted one or more times with substituents selected independently from a halogen atom, Alk group, OAlk group, $S(O)_n$Alk group or $OS(O)_n$Alk group;

$R_6$ represents a hydrogen atom or a $(C_1-C_3)$-alkyl;

n represents 0, 1 or 2; and

Alk represents a $(C_1-C_4)$-alkyl, unsubstituted or substituted one or more times with a fluorine atom;

with the proviso that $R_4$ and $R_5$ do not simultaneously represent a phenyl substituted with a $(C_1-C_4)$-alkoxy.

2. The compound of formula (I) according to claim 1, wherein —X— represents a —CO— radical and the substituents $R_1$ to $R_5$ are as defined in claim 1.

3. The compound of formula (I) according to claim 1, wherein —X— represents an —$SO_2$— radical and the substituents $R_1$ to $R_5$ are as defined in claim 1.

4. The compound of formula (I) according to claim 1, wherein —X— represents a —$CON(R_6)$— radical and the substituents $R_1$ to $R_6$ are as defined in claim 1.

5. The compound of formula (I) according to claim 1, wherein:
X represents a —CO— group, an —$SO_2$— group, a —$CON(R_6)$— group;
$R_1$ represents:
  1-ethylpropyl or 1-propylbutyl;
  cyclopentyl, cyclohexyl, cycloheptyl or 2-norbornyl;
  phenyl, 4-bromophenyl, 3-chlorophenyl, 4-chlorophenyl, 2-fluorophenyl, 3-fluorophenyl, 3,5-difluorophenyl, 4-tert-butylphenyl, 3,5-dimethylphenyl, 3-methoxyphenyl, 4-(diethylamino)phenyl, 3-(trifluoromethyl)phenyl, 4-(trifluoromethyl)phenyl, 2-chloro-4-trifluoromethyl)phenyl, 2-nitro-4-(trifluoromethyl)phenyl, 2-bromo-4-(trifluoromethyl)phenyl, 2-fluoro-5-(trifluoromethyl)phenyl, 4-fluoro-3-(trifluoromethyl)phenyl, 2-chloro-5-(trifluoromethyl)phenyl, 4-(difluoromethoxy)phenyl, biphenyl-2-yl, 3-phenoxyphenyl, 4-phenoxyphenyl or 4-(1H-pyrrol-1-yl)phenyl;
  3-(trifluoromethyl)benzyl; benzhydrylmethyl; or
  2-thienyl, 5-chloro-2-thienyl, 5-bromo-2-furyl, 3-tert-butyl-1-ethyl-1H-pyrazol-5-yl, 1H-indol-2-yl or 1-methyl-1H-indol-2-yl;
$R_2$ represents a hydrogen atom;
$R_3$ represents a hydrogen atom or methyl;
$R_4$ represents 4-bromophenyl, 4-chlorophenyl or 4-methoxyphenyl;
$R_5$ represents 2,4-dichlorophenyl; and
$R_6$ represents a hydrogen atom.

6. The compound of formula (I) according to claim 1, wherein:
X represents —CO— or —$SO_2$— group;
$R_1$ represents:
  3-(trifluoromethyl)phenyl, 4-(trifluoromethyl)phenyl, 2-chloro-4-(trifluoromethyl)phenyl, 3-phenoxyphenyl or 4-(1H-pyrrol-1-yl)phenyl; or benzhydrylmethyl;
$R_2$ represents a hydrogen atom;
$R_3$ represents a hydrogen atom or methyl;
$R_4$ represents 4-bromophenyl or 4-methoxyphenyl; and
$R_5$ represents 2,4-dichlorophenyl.

7. The compound of formula (I) according to claim 1 selected from:
N-[[5-(4-bromophenyl)-4-(2,4-dichlorophenyl)pyrimidin-2-yl]methyl]-3-(trifluoromethyl)benzenesulfonamide;
N-[[5-(4-bromophenyl)-4-(2,4-dichlorophenyl)pyrimidin-2-yl]methyl]-4-(trifluoromethyl)benzenesulfonamide;
N-[[4-(2,4-dichlorophenyl)-5-(4-methoxyphenyl)pyrimidin-2-yl]methyl]-4-(1H-pyrrol--yl)benzamide;
N-[[5-(4-bromophenyl)-4-(2,4-dichlorophenyl)pyrimidin-2-yl]methyl]-3,3-diphenylpropanamide;
N-[[5-(4-bromophenyl)-4-(2,4-dichlorophenyl)-6-methylpyrimidin-2-yl]methyl]-3,3-diphenylpropanamide;
N-[[5-(4-bromophenyl)-4-(2,4-dichlorophenyl)-6-methylpyrimidin-2-yl]methyl]-3-(trifluoromethyl)benzenesulfonamide;
N-[[5-(4-bromophenyl)-4-(2,4-dichlorophenyl)-6-methylpyrimidin-2-yl]methyl]-4-(trifluoromethyl)benzenesulfonamide;
N-[[5-(4-bromophenyl)-4-(2,4-dichlorophenyl)-6-methylpyrimidin-2-yl]methyl]-2-chloro-4-(trifluoromethyl)benzenesulfonamide; and
N-[[5-(4-bromophenyl)-4-(2,4-dichlorophenyl)-6-methylpyrimidin-2-yl]methyl]-3-phenoxybenzenesulphonamide.

8. A method of preparation of a compound of formula (I) according to claim 1, comprising:
reacting a compound of formula (II):

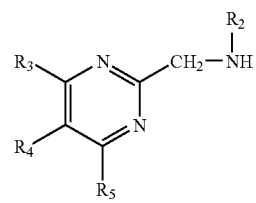

(II)

in which $R_2$, $R_3$, $R_4$ and $R_5$ are as defined in claim 1 either with an acid of formula (III) or a functional derivative thereof:

HOOC—$R_1$  (III)

in which $R_1$ is as defined in claim 1, when it is necessary to prepare a compound of formula (I) in which —X— represents a —CO— group;
or with a sulfonyl halide of formula (IV):

Hal-$SO_2$—$R_1$  (IV)

in which $R_1$ is as defined in claim 1, and Hal represents a halogen atom, when it is necessary to prepare a compound of formula (I) in which —X— represents an —$SO_2$— group;
or with a haloformate of formula (V):

HalCOOAr  (V)

in which Hal represents a halogen atom and Ar represents a phenyl or a 4-nitrophenyl to obtain an intermediate of formula (VI):

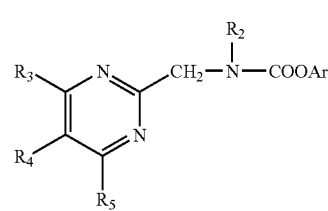

(VI)

in which $R_2$, $R_3$, $R_4$ and $R_5$ are as defined in claim 1, which is then reacted with an amine of formula (VII):

HN($R_6$)$R_1$  (VII)

in which $R_1$ and $R_6$ are as defined in claim 1, when it is necessary to prepare a compound of formula (I) in which —X— represents a —$CON(R_6)$— group.

9. A pharmaceutical composition comprising a compound of formula (I) according to claim 1 in combination with at least one pharmaceutical acceptable excipient.

10. A pharmaceutical composition comprising a compound of formula (I) according to claim 2 in combination with at least one pharmaceutically acceptable excipient.

11. A pharmaceutical composition comprising a compound of formula (I) according to claim 3 in combination with at least one pharmaceutically acceptable excipient.

12. A pharmaceutical composition comprising a compound of formula (I) according to claim 4 in combination with at least one pharmaceutically acceptable excipient.

13. A pharmaceutical composition comprising a compound of formula (I) according to claim 5 in combination with at least one pharmaceutically acceptable excipient.

14. A pharmaceutical composition comprising a compound of formula (I) according to claim 6 in combination with at least one pharmaceutically acceptable excipient.

15. A pharmaceutical composition comprising a compound of formula (I) according to claim 7 in combination with at least one pharmaceutically acceptable excipient.

16. A method of treatment of obesity comprising administering to a patient in need of said treatment a therapeutically effective amount of a compound of formula (I) according to claim 1.

* * * * *

UNITED STATES PATENT AND TRADEMARK OFFICE
CERTIFICATE OF CORRECTION

| | | |
|---|---|---|
| PATENT NO. | : 7,541,361 B2 | Page 1 of 1 |
| APPLICATION NO. | : 11/968855 | |
| DATED | : June 2, 2009 | |
| INVENTOR(S) | : Francis Barth et al. | |

It is certified that error appears in the above-identified patent and that said Letters Patent is hereby corrected as shown below:

On the title page, item (54), in column 1, in "Title", line 1, delete "N-[4,5-" and insert -- N-[(4,5- --, therefor.

On the title page, item (75), in column 1, in "Inventors", line 3, delete "Fese" and insert -- Fesc --, therefor.

In column 1, line 1, delete "N-[4,5-" and insert -- N-[(4,5- --, therefor.

In column 1, line 4, below Title insert -- Related U.S. Application Data --, as a heading.

In column 49, line 46, delete "Tourrette" and insert -- Tourette --, therefor.

In column 51, line 40, delete "tertalol," and insert -- tetralol, --, therefor.

In column 52, line 28, delete "phosphase-1B)," and insert -- phosphatase-1B), --, therefor.

In column 54, line 44-45, in claim 1, delete "($C_1$-$C_4$-alkyl, a ($C_1$-$C_4$-alkoxy," and insert -- ($C_1$-$C_4$)-alkyl, a ($C_1$-$C_4$)-alkoxy, --, therefor.

In column 55, line 13, in claim 5, delete "2-norbomyl;" and insert -- 2-norbornyl; --, therefor.

In column 55, line 14, in claim 5, delete "3 -chiorophenyl," and insert -- 3-chlorophenyl, --, therefor.

In column 55, line 14-15, in claim 5, delete "4-chiorophenyl," and insert -- 4-chlorophenyl, --, therefor.

In column 55, line 16, in claim 5, delete "3,5-dimethyiphenyl," and insert -- 3,5-dimethylphenyl, --, therefor.

In column 55, line 19, in claim 5, delete "2-chloro-4-trifluoromethyl)phenyl," and insert -- 2-chloro-4-(trifluoromethyl)phenyl, --, therefor.

In column 55, line 57, in claim 7, delete "(1H-pyrrol–yl)" and insert -- (1H-pyrrol-yl) --, therefor.

Signed and Sealed this
Thirty-first Day of May, 2011

David J. Kappos
*Director of the United States Patent and Trademark Office*